United States Patent [19]

Jung et al.

[11] Patent Number: 5,441,949
[45] Date of Patent: Aug. 15, 1995

[54] CARBAPENEM ANTIBIOTIC COMPOUNDS

[75] Inventors: Frederic H. Jung, Rilly La Montagne; Jean-Claude Arnould, Cormontreuil, both of France

[73] Assignee: Zeneca Limited, London, England

[21] Appl. No.: 307,048

[22] Filed: Sep. 16, 1994

Related U.S. Application Data

[63] Continuation of Ser. No. 86,836, Jul. 7, 1993, abandoned.

[30] Foreign Application Priority Data

Jul. 21, 1992 [EP] European Pat. Off. ............ 92402105

[51] Int. Cl.⁶ .................. A01N 43/00; A61K 31/395; C07D 487/04
[52] U.S. Cl. ................................. 514/210; 540/350; 540/200
[58] Field of Search .......................... 540/350; 514/210

[56] References Cited

U.S. PATENT DOCUMENTS

| | | |
|---|---|---|
| 4,206,219 | 6/1980 | Christensen et al. . |
| 4,208,422 | 6/1980 | Christensen et al. . |
| 4,218,462 | 8/1980 | Christensen et al. . |
| 4,232,036 | 11/1980 | Christensen et al. . |
| 4,963,544 | 10/1990 | Murata et al. . |
| 5,194,624 | 3/1993 | Murata et al. . |
| 5,215,983 | 6/1993 | Murata et al. . |

FOREIGN PATENT DOCUMENTS

| | | |
|---|---|---|
| 0126587 | 11/1984 | European Pat. Off. . |
| 0160391 | 11/1985 | European Pat. Off. . |
| 0182213 | 5/1986 | European Pat. Off. . |
| 0243686 | 11/1987 | European Pat. Off. . |
| 343499 | 11/1989 | European Pat. Off. . |
| 0443883 | 8/1991 | European Pat. Off. . |
| 0472062 | 2/1992 | European Pat. Off. . |
| 0518558 | 12/1992 | European Pat. Off. . |
| 60-233076 | 11/1985 | Japan . |
| 9217481 | 10/1992 | WIPO . |

*Primary Examiner*—Johann Richter
*Assistant Examiner*—Rebecca Cook
*Attorney, Agent, or Firm*—Cushman Darby & Cushman

[57] ABSTRACT

The present invention relates to carbapenems and provides a compound of the formula (I)

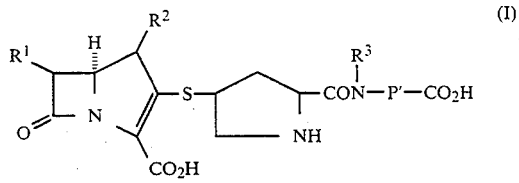

wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
$P^1$ is of the formula:

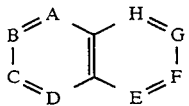

and one or two of A,B,C,D,E,F,G and H, are nitrogen and the remainder are CH; and P is bonded to the nitrogen of the linking carbamoyl group by a carbon atom, in either ring, is substituted by the carboxy group on a carbon atom, in either ring, and is optionally further substituted, by up to three substitutents, on a carbon atom, in either ring; or a pharmaceutically acceptable salt or in vivo hydrolysable ester thereof. Processes for their preparation, intermediates in their preparation, their use as therapeutic agents and pharmaceutical compositions containing them are also described.

8 Claims, No Drawings

CARBAPENEM ANTIBIOTIC COMPOUNDS

This is a continuation of application Ser. No. 08/086,836, filed on Jul. 7, 1993, which was abandoned upon the filing hereof.

The present invention relates to carbapenems and in particular to such compounds containing a carboxy substituted bicyclic nitrogen containing ring system. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first, and so far the only, carbapenem to be commercially marketed is imipenem (N-formimidoyl thienamycin). This compound has a broad spectrum of antibacterial activity.

The present invention provides compounds with a broad spectrum of antibacterial activity including both Gram positive and negative, aerobic and anaerobic bacteria. They exhibit good stability to beta-lactamases. In addition representative compounds of this invention exhibit favourable pharmacokinetics.

The carbapenem derivatives referred to herein are named in accordance with the generally accepted semi-systematic nomenclature:

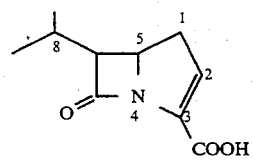

Accordingly the present invention provides a compound of the formula (I)

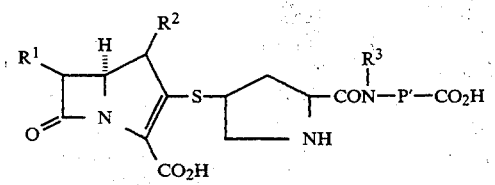

wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
P is of the formula:

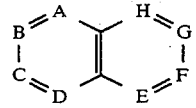

and one or two of A,B,C,D,E,F,G and H, are nitrogen and the remainder are CH; and $P^1$ is bonded to the nitrogen of the linking carbamoyl group by a carbon atom, in either ring, is substituted by the carboxy group on a carbon atom, in either ring, and is optionally further substituted, on a carbon atom, in either ring, by up to three substituents selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, $C_{1-4}$alkylS(O)$_n$— (wherein n is 0–2), $C_{1-4}$alkanoylamino, $C_{1-4}$alkanoyl(N—$C_{1-4}$alkyl)amino, carbamoyl, $C_{2-6}$alkenyloxy, $C_{1-4}$alkylcarbamoyl and di-$C_{1-4}$alkylcarbamoyl; or a pharmaceutically acceptable salt or in vivo hydrolysable ester thereof.

The term alkyl includes all straight and branched chain structures, for example, $C_{1-4}$alkyl includes n-butyl and 2-methylpropyl.

Preferably $R^1$ is 1-hydroxyethyl.

$R^2$ is hydrogen or $C_{1-4}$alkyl for example methyl, ethyl, n-propyl, 1-methylethyl and n-butyl.

Preferably $R^2$ is hydrogen or methyl and in particular $R^2$ is methyl.

Particular bicyclic ring systems for P are quinoline, isoquinoline, phthalazine, quinoxaline, quinazoline, cinnoline, 1,8-naphthyridine, 1,7-naphthyridine, 1,6-naphthyridine, 1,5-naphthyridine, 2,7-naphthyridine and 2,6-naphthyridine.

Preferably $P^1$ is quinoline, isoquinoline, quinoxaline or quinazoline. In another aspect $P^1$ is quinoline, quinoxaline or quinazoline. Most preferably $P^1$ is quinoline.

$R^3$ is hydrogen or $C_{1-4}$alkyl for example methyl, ethyl, n-propyl, 1-methylethyl and n-butyl.

Preferably $R^3$ is hydrogen or methyl.

Most preferably $R^3$ is hydrogen.

Suitable substituents for the bicyclic ring system include, for example:
for halo: fluoro, chloro, bromo and iodo;
for $C_{1-4}$alkyl: methyl, ethyl, propyl, 1-methylethyl, butyl and 2-methylpropyl;
for $C_{1-4}$alkoxy: methoxy, ethoxy, propoxy, 1-methylethoxy, butoxy and 2-methylpropoxy;
for $C_{1-4}$alkylcarbamoyl: methylcarbamoyl, ethylcarbamoyl and propylcarbamoyl;
for di-$C_{1-4}$alkylcarbamoyl: dimethylcarbamoyl and diethylcarbamoyl;
for $C_{1-4}$alkylamino: methylamino, ethylamino and propylamino;
for di-$C_{1-4}$alkylamino: dimethylamino, diethylamino and methylethylamino;
for $C_{1-4}$alkylS(O)$_n$—: methylthio, methylsulfinyl and methylsulfonyl;
for $C_{1-4}$alkanoylamino: acetamido and propionamido;
for $C_{1-4}$alkanoyl(N—$C_{1-4}$alkyl)amino: N-methylacetamido and N-ethylacetamido;
for $C_{2-6}$alkenyloxy: allyloxy and vinyloxy.

Preferably when $P^1$ is optionally substituted, the optional substituents are selected from halo, cyano, $C_{1-4}$alkyl, nitro, carboxy, hydroxy, $C_{1-4}$alkoxy, carbamoyl, amino, trifluoromethyl and allyloxy.

The present invention covers all epimeric, diastereoisomeric and tautomeric forms of the compounds of the formula (I) wherein the absolute stereochemistry at the 5-position is as illustrated in formula (I). When a bond is represented as a wedge, this indicates that in three dimensions the bond would be coming forward out of the paper and when a bond is represented as hatched, this indicates that in three dimensions the bond would be going back into the paper. The compounds of the formula (I) have a number of other centres of optical activity, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring:

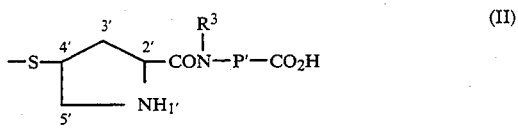

Preferred compounds are those in which the beta-lactam protons are in trans configuration with respect to one another. When $R^1$ is 1-hydroxyethyl or 1-fluoroethyl it is preferred that the 8-substituent has the R-configuration. Thus a preferred class of compounds is that of the formula (III):

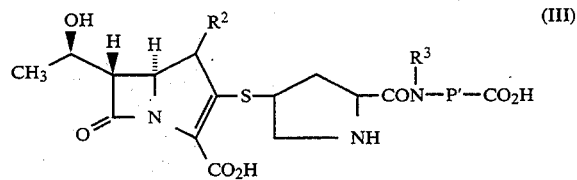

and pharmaceutically acceptable salts and in vivo hydrolysable esters thereof, wherein $P^1$, $R^2$, $R^3$ and optional substituents on $P^1$ are as hereinbefore defined.

When $R^2$ is $C_{1-4}$alkyl for example methyl it is preferred that the compound is in the form of the 1R configuration.

Preferred compounds are those in which the pyrrolidine ring has the following absolute stereochemistry at the 2'- and 4'-positions:

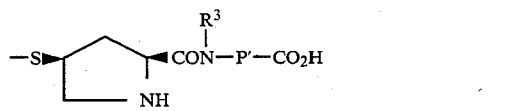

A suitable class of compounds of the present invention is that of the formula (IV):

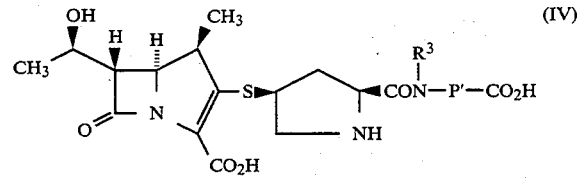

and pharmaceutically acceptable salts and in vivo hydrolysable esters thereof;
wherein $P^1$, $R^3$ and optional substituents on $P^1$ are as defined hereinbefore in formula (I).

In another aspect a suitable class of compounds are the compounds of the formula (IV) wherein $R^3$ is hydrogen, methyl or ethyl; and $P^1$ and optional substituents on $P^1$ are as defined hereinabove in formula (I).

In yet another aspect a suitable class of compounds is that of the compounds of the formula (IV) wherein $P^1$ is optionally further substituted by one or two substituents selected from methyl, ethyl, hydroxy, carboxy, cyano, fluoro, chloro, bromo, carbamoyl, nitro, methoxy, ethoxy, propoxy and allyloxy; and $P^1$ and $R^3$ are as defined hereinbefore in formula (I).

A particular class of compounds of the present invention is that of the formula (IV) wherein:
$R^3$ is hydrogen or methyl;
$P^1$ is as hereinabove defined in formula (I);
and $P^1$ is optionally further substituted by one or two substituents selected from methyl, ethyl, hydroxy, carboxy, cyano, chloro, bromo, nitro, methoxy, ethoxy and allyloxy.

A preferred class of compounds of the present invention is that of the formula (IV) wherein:
$R^3$ is hydrogen;
$P^1$ is as hereinabove defined in formula (I);
and $P^1$ is optionally further substituted by one or two substituents selected from methyl, hydroxy, chloro, carboxy and allyloxy.

A more preferred class of compounds of the present invention is that of the formula (IV) wherein:
$R^3$ is hydrogen;
$P^1$ is as hereinabove defined in formula (I);
and $P^1$ is not further substituted.

Particular compounds of the present invention are, for example, the following compounds of the formula (IV):

(1R,5S,6S,8R,2'S,4'S)-2-(2-(8-carboxyquinol-6-ylcarbamoyl)pyrrolidin-4-ylthio)-6-(1-hydroxyethyl)-1-methylcarbapenem-3-carboxylic acid; and (1R,5S,6S,8R,2'S,4'S)-2-(2-(6-carboxyquinol-8-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(7-carboxyquinol-5-ylcarbamoyl)pyrrolidin-4-ylthio)-6-(1-hydroxyethyl)-1-methylcarbapenem-3-carboxylic acid;

(1R,5S 6S 8R,2'S,4'S)-2-(2-(3-carboxyquinol-2-ylcarbamoyl)pyrrolidin-4-ylthio)-6-(1-hydroxyethyl)-1-methylcarbapenem-3-carboxylic acid:

(1R,5S,6S,8R,2'S,4'S)-2-(2-(2-carboxyquinol-4-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-6-allyloxyquinol-2-ylcarbamoyl)-pyrrolidin-4-ylthio)-6-(1-hydroxyethyl)-1-methylcarbapenem-3-carboxylic acid;

(1R,5S,6S,8R,2'S,4'S)-2-(2-(2-carboxyquinol-6-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(4-carboxyquinol-8-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(4-carboxyquinol-5-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxyquinol-8-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxyquinol-5-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(4-carboxyquinol-2-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(7-carboxy-2,3-dimethylquinoxalin-5-ylcarbamoyl)pyrrolidin-4-ylthio)-6-(1-hydroxyethyl)-1-methylcarbapenem-3-carboxylic acid;

(1R, 5S,6S,8R,2'S,4'S)-2-(2-(4-carboxyquinazolin-2-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxyisoquinol-5-ylcarbamoyl)-pyrrolidin-4-ylthio)-6-(1-hydroxyethyl)-1-methylcarbapenem-3-carboxylic acid;

and pharmaceutically acceptable salts and in vivo hydrolysable esters thereof.

Suitable pharmaceutically acceptable salts include acid addition salts such as hydrochloride, hydrobromide, citrate, maleate and salts formed with phosphoric and sulfuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or aminoacids, for example, lysine.

For the avoidance of doubt there may be one, two, three or four salt-forming cations depending on the number of carboxylic acid functions and valency of said cations.

Preferred pharmaceutically acceptable salts are sodium and potassium salts. However, to facilitate isolation of the salt during preparation, salts which are less soluble in the chosen solvent may be preferred, whether pharmaceutically acceptable or not.

In vivo hydrolysable esters are those pharmaceutically acceptable esters that hydrolyse in the human body to produce the parent hydroxy or carboxy compound. Such esters can be identified by administering, eg. intravenously to a test animal, the compound under test and subsequently examining the test animal's body fluids. Suitable in vivo hydrolysable esters for hydroxy include acetoxy, propionyloxy, pivaloyloxy, $C_{1-4}$alkoxycarbonyloxy for example ethoxycarbonyloxy, phenylacetoxy and phthalidyl. Suitable in vivo hydrolysable esters for carboxy include $C_{1-6}$alkoxymethyl esters for example methoxymethyl; $C_{1-6}$alkanoyloxymethyl esters for example pivaloyloxymethyl; $C_{3-8}$cycloalkoxycarbonyloxy$C_{1-6}$alkyl, for example 1-cyclohexyloxycarbonyloxyethyl; 1,3-dioxolen-2-onylmethyl esters for example 5-methyl1,3-dioxolen-2-onylmethyl; phthalidyl esters and $C_{1-6}$alkoxycarbonyloxyethyl esters for example 1-ethoxycarbonyloxyethyl and may be formed at any carboxy group in the compounds of this invention.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids such as betamipron (also see EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable composition containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, as as follows:

| Composition 1 | |
|---|---|
| Compound of Example 1 | 50 mg |
| Composition 2 | |
| Compound of Example 1 | 50 mg |
| Glycine | 31 mg |

Further specific examples of compositions are as above, but where the compound of example 1 is replaced by any one of examples 2 to 15.

The pharmaceutical compositions of the invention will normally be administered to man in order to combat infections caused by bacteria, in the same general manner as that employed for imipenem due allowance being made in terms of dose levels for the pharmacokinetics of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g. of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V) wherein P is optionally further substituted as in formula (I):

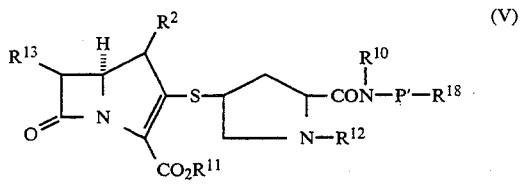

wherein $P^1$ is as hereinbefore defined; $R^2$ is as hereinbefore defined; $R^{10}$ is a group $R^3$ or an amino protecting group; $R^{13}$ is a group $R^1$, protected hydroxymethyl or 1-(protected hydroxy)ethyl; $R^{11}$ is hydrogen or a carboxy protecting group; $R^{12}$ is hydrogen or an amino protecting group, $R^{18}$ is carboxy or a protected carboxy group and wherein any optional substituent on $P^1$ is optionally protected; and wherein at least one protecting group is present; and thereinafter if necessary;

(i) forming a pharmaceutically acceptable salt,
(ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The compounds of the formula (V) are novel and form another aspect of the invention.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); diaryl(lower alkyl)silyl groups (eg t-butyldiphenylsilyl); and (2–6C)alkenyl groups (eg allyl and vinylethyl).

Methods particularly appropriate for the removal of carboxyl protecting groups include for example acid-, base-, metal- or enzymically-catalysed hydrolysis, for groups such as p-nitrobenzyloxycarbonyl, hydrogenation and for groups such as o-nitrobenzyloxycarbonyl, photolytically.

Examples of hydroxyl protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, t-nitrobenzyloxycarbonyl); tri lower alkylsilyl (eg trimethylsilyl, t-butyldimethylsilyl); diaryl(lower alkyl)silyl groups (eg t-butyldiphenylsilyl) and aryl lower alkyl (eg benzyl) groups.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); diaryl(lower alkyl)silyl group (eg t-butyldiphenylsilyl); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

In another aspect; of the present invention the compounds of the formulae (I) and (V) may be prepared by
a) reacting compounds of the formulae (VI) and (VII):

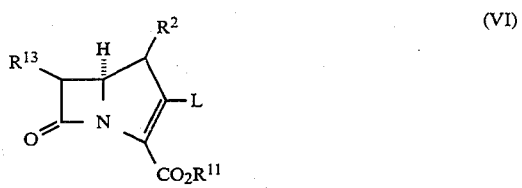

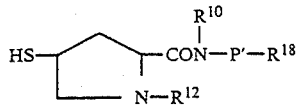 (VII)

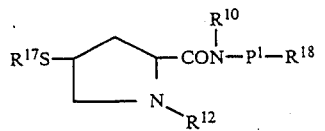 (IX)

wherein $P^1$, $R^2$, $R^{10}$, $R^{11}$, $R^{12}$, $R^{13}$ and $R^{18}$ are as hereinbefore defined, $P^1$ is optionally substituted as hereinbefore defined and L is a leaving group, or b) cyclising a compound of the formula (VIII):

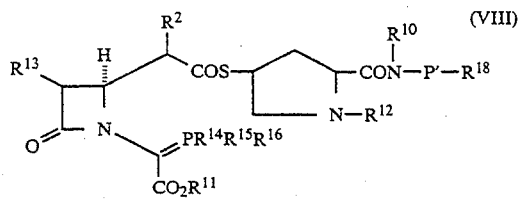 (VIII)

wherein $P^1$, $R^2$, $R^{10}$, $R^{11}$, $R^{12}$, $R^{13}$ and $R^{18}$ are as hereinbefore defined, $P^1$ is optionally substituted as hereinbefore defined and $R^{14}$, $R^{15}$ and $R^{16}$ are independently selected from $C_{1-6}$alkoxy, aryloxy, di-$C_{1-6}$alkylamino and diarylamino or any two of $R^{14}$-$R^{16}$ represent o-phenylenedioxy or one of $R^{14}$-$R^{16}$ is $C_{1-4}$alkyl, allyl, benzyl or phenyl and the other two values are independently selected from $C_{1-4}$alkyl, trifluoromethyl or phenyl, wherein any phenyl group is optionally substituted with $C_{1-3}$alkyl or $C_{1-3}$alkoxy; and wherein any functional group is optionally protected and thereinafter if necessary:

(i) removing any protecting groups;
(ii) forming a pharmaceutically acceptable salt;
(iii) esterifying to form an in vivo hydrolysable ester.

Suitably in the compound of the formula (VI), L is the reactive ester of a hydroxy group such as a sulphonate (for example $C_{1-6}$alkanesulphonyloxy, trifluoromethanesulphonyloxy, benzenesulphonyloxy, toluenesulphonyloxy), a phosphoric ester (for example a diarylphosphoric ester such as diphenylphosphoric ester) or L is a halide (for example chloride). In an alternative L is a sulphoxide for example —SOCH=CH—NH—COCH$_3$ which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between −25° C. and ambient. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

wherein $P^1$, $R^{10}$, $R^{12}$ and $R^{18}$ are as hereinbefore defined, $P^1$ is optionally substituted as hereinbefore defined and $R^{17}$ is a protecting group, for example $C_{1-6}$alkanoyl or $C_{1-6}$alkoxycarbonyl. Preferred values for $R^{17}$ are acetyl and t-butoxycarbonyl. The compounds of the formula (IX) can be converted to the compounds of the formula (VII) by standard methods of deprotection, for example acetyl groups can be removed by basic hydrolysis in aqueous alkanol, alkenol for example with methylamine in ethanol.

The compounds of the formula (IX) are novel and form another aspect of the present invention.

The compounds of the formula (IX) may be prepared by the reaction of an activated derivative of a compound of the formula (X), which may be formed in situ, with a compound of the formula (XI):

$R^{17}S-\underset{\underset{R^{12}}{N}}{\underset{|}{\square}}-CO_2H$ (X)

$\underset{|}{R^{10}} \\ HN-P^1-R^{18}$ (XI)

wherein $P^1$, $R^{10}$, $R^{12}$, $R^{17}$ and $R^{18}$ are as hereinbefore defined and $P^1$ is optionally substituted as hereinbefore defined. Activated derivatives of the compound of the formula (X) include acid halides, anhydrides and 'activated' esters such as 1H-benzol-1,2,3-triazol-1-yl, pentafluorophenyl and 2,4,5-trichlorophenyl esters or the benzimidazol-2-yl ester of the thiocarboxylic acid corresponding to (X). The reaction of the compounds of the formulae (X) and (XI) is performed under standard methods, for example in the presence of sulphonyl chloride at ambient temperature.

The compounds of the formulae (X) and (XI) are prepared by standard methods known to the skilled chemist such as the methods of the Examples hereinafter, the methods described in EP-A-126587 or by methods analogous or similar thereto. For example, bicyclic rings of the formula $P^1$ substituted with a methyl group on a ring carbon atom are converted to compounds of the formula (XI) by oxidating the methyl group to a carboxy group, nitrating the ring to introduce a nitro group and reducing the nitro group to an amino group. The oxidation, nitration and reduction steps involve standard methods known in the art.

Suitably, in the compounds of the formula (VIII), $R^{14}$, $R^{15}$ and $R^{16}$ are independently selected from $C_{1-6}$ alkoxy such as methoxy, ethoxy, isopropoxy, n-propoxy or n-butoxy; aryloxy such as optionally phenoxy; di-$C_{1-6}$alkylamino such as dimethylamino or diethylamino; diarylamino such as diphenylamino or any two of $R^{14}$-$R^{16}$ represent o-phenylenedioxy. Preferably each of $R^{14}$-$R^{16}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

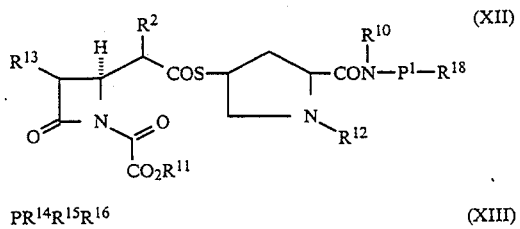

$PR^{14}R^{15}R^{16}$ (XIII)

wherein $P^1$, $R^2$, $R^{10}$, $R^{11}$–$R^{16}$, and $R^{18}$ are as hereinbefore defined and $P^1$ is optionally substituted as hereinbefore defined. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example 60°–150° C.

The compounds of the formula (XII) may be prepared by a number of methods known in the art. For example the compounds of the formula (XII) may be prepared by the acylation of a compound of the formula (XIV):

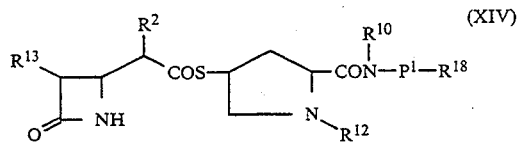

wherein $P^1$, $R^2$, $R^{10}$, $R^{12}$, $R^{13}$, and $R^{18}$ are as hereinbefore defined and $P^1$ is optionally substituted as hereinbefore defined with a compound of the formula (XV):

Cl—CO—COOR$^{11}$ (XV)

wherein $R^{11}$ is as hereinbefore defined.

The compounds of the formula (XIV) may be prepared by reacting compounds of the formulae (XVI) and (VII):

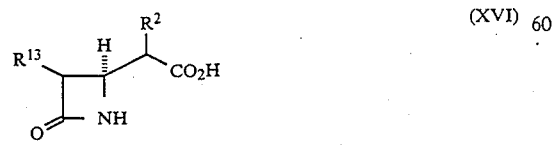

wherein $R^2$ and $R^{13}$ are as hereinbefore defined. The compounds of the formula (XVI) are known in the art and may be reacted with the compounds of the formula (VII) under conventional acylation methods known in the art.

Compounds of the formulae (VII), (XII) and (XIV) are novel and, as such, form another aspect of this invention.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and in general particularly good pharmacekinetics, especially as regards half life. In general compounds show significant improvement over imipenem.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inoculum size of $10^4$ CFU/spot.

| ORGANISM | MIC (μg/ml) EXAMPLE 1 |
|---|---|
| S. aureus Oxford | 0.13 |
| E. coli DCO | 0.03 |
| P. morganii I + 001 | 0.03 |
| Enterobacter cloacae P99- | 0.03 |
| B. fragilis AMP S | 0.50 |

In the following examples, which are representative of the scope:
(a) NMR spectra were taken at 200 MHz or 400 MHz in DMSO-d$_6$/CD$_3$COOD unless otherwise stated;
(b) allyloxy means the propen-1-yloxy group —OCH$_2$CH=CH$_2$;
(c) THF means tetrahydrofuran;
(d) DMF means dimethylformamide;
(e) DMSO means dimethylsulphoxide;
(f) DIAD means diisopropyldiazodicarboxylate;
(g) DEAD means diethylazodicarboxylate
(h) EEDQ means N-ethoxycarbonyl-2-ethoxy-1,2-dihydroquinoline;
(i) TFA means trifluoroacetic acid;

(j) evaporation of solvents was carried out under reduced pressure;
(k) HPLC means high pressure liquid chromatography; and
(l) temperatures are given in degrees centigrade.

EXAMPLE 1

(1R,5S,6S,8R,2'S,4'S)
2-(2-(8-Carboxyquinol-6-ylcarbamoyl)pyrrolidin-4-ylthio)-6-(1-hydroxyethyl)-1-methylcarbapenem-3-carboxylic Acid Disodium Salt To a solution of allyl (1R,5S,6S,8R,2'S,4'S)-2-(1-allyloxycarbonyl-2-(8-allyloxycarbonylquinol-6-ylcarbamoyl) pyrrolidin-4-ylthio)-6-(1-hydroxyethyl)-1-methylcarbapenem-3-carboxylate (216 mg; 0.31 mm) in $CH_2Cl_2$ (7 ml), was added a 0.47M aqueous solution of $NaHCO_3$ (7.8 ml), N-methylaniline (135 μl; 1.24 mM) and tetrakistriphenylphosphine palladium (72 mg; 0.062 mM). After stirring for 1 hour the aqueous layer was separated and purified on reverse phase silica (Nucleosil $C_{18}$) using a gradient of acetonitrile in water (0–10%) to give after freeze-drying the title compound as a foam (30 mg; 16.6%).

NMR: δ1.10–1.21 (m, 6H); 1.71–1.88 (m, 1H); 2.60–2.72 (m, 1H); 2.76–2.88 (m, 1H); 3.20 (dd, 1H); 3.37–3.5 (m, 2H); 3.60–3.73 (m, 1H); 3.92–4.05 (m, 2H); 4.17 (dd, 1H); 7.75 (dd, 1H); 8.65 (d, H); 8.75 (d, 1H); 8.81 (d, 1H); 8.97 (d, 1H) MS (+ve FAB): 571 (MH+).

The starting material was prepared as follows:

A mixture of 2-amino-5-nitrobenzoic acid (4 g, 22 mM), glycerol (8 g), arsenic acid (80% in water) (20 g), and sulphuric acid (65%) (36 ml) was heated at reflux for 3.5 hours. After addition of water (100 ml), the pH was adjusted to 8 with concentrated ammonia and then to 3.5 with acetic acid. The resulting precipitate was filtered and dried to give 8-carboxy-6-nitroquinoline (4 g; 83%).

NMR (DMSO-$d_6$): δ7.75 (dd, 1H); 8.72 (dd, 1H); 9.00 (d, 1H); 9.07 (d, 1H); 9.37 (d, 1H).

To a suspension of 8-carboxy-6-nitroquinoline (4 g; 18 mM) in methanol (70 ml) was added $SnCl_2$ (20.4 g; 90 mM). The mixture was heated to, and maintained at 40° C. until dissolution of the insoluble. After evaporation of the solvent, the residue was taken-up in a 2M aqueous solution of NaOH and purified by subjecting to chromatography on Dowex 1X2 Resin. After basification (pH3) with concentrated $NH_4OH$ the resulting solid was further purified by subjecting to chromatography on HP20SS resin, eluting with MeOH/$H_2O$—AcOH 1% (30.70) to give 6-amino-8-carboxyquinoline (1.2 g, 35.5%)

NMR(DMSO-$d_6$):δ7.13 (d, 1H); 7.57 (dd, 1H); 8.11 (d, 1H); 8.34 (dd, 1H); 8.67 (d, 1H).

Preparation of the side-chain pyrrolidin-4-ylthioacetate:

To a solution of (2S,4S)-1-allyloxycarbonyl-2-carboxypyrrolidin-4-ylthioacetate (1.75 g, 6.4 mM) in $CH_2Cl_2$ (15 ml) was added $SOCl_2$ (5 ml; 68.5 mM). After stirring at ambient temperature for 3 hours, the solvent was evaporated and dried under reduced pressure. The product was dissolved in $CH_2Cl_2$ (25 ml) and the resulting solution added dropwise to a solution of 6-amino-8-carboxyquinoline (1.2 g; 6.3 mM), N-ethyl diisopropylamine (11 ml, 56.7 mM) and trimethylethylchloride (2 m; 1.57 mM). The mixture was stirred at ambient temperature overnight. After extraction with methylene chloride, the material was purified by subjecting to chromatography on HP20SS and eluting with a gradient of acetonitrile (0–4%) in $H_2O$/AcOH 1% to give (2S,4S)-1-allyloxycarbonyl-2-(8-carboxyquinol-6-ylcarbamoyl) pyrrolidin-4-ylthioacetate (870 mg; 31%).

NMR (DMSO-$d_6$): δ1.85–2.10 (m, 1H); 2.31 (S, 3H); 2.65–2.92 (m, 1H); 3.25–3.56 (m, 1H); 3.86–4.11 (m, 2H); 4.31–4.70 (m, 3H); 5.00–5.40 (m, 2H); 5.70–6.04 (m, 1H); 7.75 (dd, 1H); 8.63 (d, 1H); 8.76 (d, 2H); 8.96 (d, 1H).

Synthesis of (2S,4S)-1-allyloxycarbonyl-2-(8-allyloxycarbonylquinol-6-ylcarbamoyl)pyrrolidin-4-ylthioacetate:

To a solution of the product of the previous step compound (380 mg; 0.85 mM) in THF (5 ml), under argon, was added triphenylphosphine (247 mg, 0.93 mM) and DIAD (186 μl; 0.93 mM). After stirring at 0° C. for 15 minutes and at ambient temperature for 30 minutes, the resulting solution was partitioned between phosphate buffer (pH7) and ethyl acetate. The organic phase was evaporated and the residue purified by subjecting to flash chromatography and eluting with ethyl acetate/petroleum ether (65/35) to give the title compound as an oil (265 mg;

NMR (DMSO $d_6$): δ1.88–2.05 (m, 1H); 2.34 (s, 3H); 2.71–2.88 (m, 1H); 3.25–3.4 (m, 1H); 3.94–4.10 (m, 2H); 4.38–4.60 (3H); 4.90 (d, 2H); 5.15–5.36 (m, 3H); 5.50 (d, 1H); 5.71–6.00 (m, 1H); 6.02–6.13 (m, 1H); 7.55 (dd, 1H); 8.11 (dd, 1H); 8.38 (d, 1H); 8.32–8.39 (m, 1H); 8.85 (d, 1H).

Allyl (1R,5R,6S,8R)-6-(1-hydroxyethyl)-1-methyl-2-diphenylphosphoryloxycarbapenem-3-carboxylate was prepared as follows:

To a solution of allyl (1R,5R,6S,8R)-6-(1-hydroxyethyl)-1-methyl-2-oxocarbapenem-3-carboxylate [prepared in situ from allyl 2-diazo-3-oxo-4-(R)-methyl-4-[(3S,4R)-3-(1-(R)-hydroxyethyl)-2-oxazetidin-4-yl]-butanoate and rhodium octanoate: see for example EP-A-208889] and di-isopropylethylamine (1.1 equivalents) in acetonitrile, at 0° C., under an argon atmosphere, was added dropwise diphenyl chlorophosphate (1.1 equivalents). The solution was stirred at ambient temperature for 30 minutes to form the corresponding 2-diphenylphosphoryloxycarbapenem.

Preparation of the protected carbapenem:

To a solution of the above thioacetate (265 mg; 0.54 mM) in ethanol (3 ml) was added at 0° C. a solution of methylamine in ethanol (5M) (329 μl; 1.62 mM). After stirring at ambient temperature for 1.5 hours, the solvent was removed by evaporation and the resulting thiol dried under vacuum, dissolved in DMF (10 ml) and added to a solution of allyl (1R,5R,6S,8R)-6-(1-hydroxyethyl)-1-methyl-2-diphenylphosphoryloxycarbapenem-3-carboxylate (270 mg; 0.54 mM), tri-n-butylphosphine (134 μl; 0.54 mM), N-ethyl diisopropylamine (187 μl; 1.08 mM) and water (9.7 μl; 0.54 mM) in DMF (10 ml). The mixture was stirred at ambient temperature for 2 hours. After evaporation of the solvent, the residue was extracted with methylene chloride and purified by subjecting to flash chromatography, eluting with ethyl acetate/$CH_3CN$ (95/5) to give allyl (1R,5S,6S,8R,2'S,4'S) (2-(1-allyloxycarbonyl-2-(8-allyloxycarbonylquinol-6-ylcarbamoyl) pyrrolidin-4-ylthio)-6-(1-hydroxyethyl)-1-methylcarbapenem-3-carboxylate as an oil (250 mg—67%).

NMR (DMSO-d$_6$): δ1.14–1.23 (m, 6H); 1.86–2.05 (m, 1H); 2.75–2.92 (m, 1H); 3.20–3.40 (m, 2H); 3.47–3.63 (m, 1H); 3.90–4.09 (m, 2H); 4.12–4.30 (m, 2H); 4.4–4.65 (m, 3H); 4.84–5.57 (m, 10H); 5.72–6.18 (m, 3H); 7.60 (m, 1H); 8.13 (s, 1H); 8.40 (dd, 1H); 8.5 (s, 1H); 8.86 (dd, 1H).

EXAMPLE 2

(1R,5S,6S,8R,2′S,4′S)-2-(2-(6-Carboxyquinol-8-ylcarbamoyl)-pyrrolidin-4-ylthio)-6-(1-hydroxyethyl)-1-methylcarbapenem-3-carboxylic Acid Disodium Salt The title compound was prepared from the corresponding diallyl protected compound using a similar method to that described in example 1. (Yield: 31%)

NMR: δ1.10–1.21 (m, 6H) 1.78–1.89 (m, 1H); 2.57–2.76 (m, 2H); 3.21 (dd, 1H); 3.41–3.48 (m, 1H); 3.53–3.66 (m, 2H); 3.92–4.0 (m, 1H); 4.04–4.12 (m, 1H); 4.17 (dd, 1H); 7.7 (dd, 1H); 8.35 (d, 1H); 8.57 (dd, 1H); 9.02 (dd, 1H); 9.24 (d, 1H). MS: +ve FAB: 571 (MH+).

The starting material was prepared as follows:

6-Carboxy-8-nitroquinoline was prepared from ethyl 4-amino-3-nitrobenzoate using the method described for 8-carboxy-6-nitroquinoline in example 1. (Yield: 61%).

NMR (DMSO-d$_6$): δ7.76 (dd, 1H); 8.57 (s, 1H); 8.72 (dd, 1H); 8.81 (s, 1H); 9.08 (dd, 1H).

To a solution of 6-carboxy-8-nitroquinoline (5.7 g; 26 mM) in THF (70 ml) was added triphenylphosphine (8.9 g; 33.8 mM), allyl alcohol (2.3 ml; 33.8 mM) and DEAD (5.35 ml; 33.8 mM). After stirring at ambient temperature for 30 minutes, the mixture was extracted with ethyl acetate and purified by subjecting to flash chromatography, eluting with ethyl acetate/petroleum ether (40/60) to give 6-allyloxycarbonyl 8-nitroquinoline (4 g; 67.7%).

NMR (CDCl$_3$): δ4.89–4.96 (m, 2H); 5.34–5.51 (m, 2H); 6.02–6.14 (m, 1H); 7.65 (dd, 1H); 8.40 (dd, 1H); 8.61 (s, 1H); 8.8 (s, 1H); 9.15 (dd, 1H).

To a solution of 6-allyloxycarbonyl-8-nitroquinoline (4 g; 15.5 mM) in methanol (80 ml) was added SnCl$_2$. (17.8 g–77.5 mM). The mixture was heated at 40° C. for 1 hour. After evaporation of the solvent, the residue was partitioned between an aqueous solution of NaHCO$_3$ (10%) and ethyl acetate. The organic phase was concentrated and purified by subjecting to flash chromatography, eluting with ethylacetate/petroleum ether (30/70) to give 8-amino-6-allyloxycarbonylquinoline (3.4 g; 96%).

NMR (CDCl$_3$): δ4.84–4.90 (m, 2H); 5.10 (s, 2H); 5.30–5.48 (m, 2H); 6.02–6.14 (m, 1H)77.43 (dd, 1H); 7.51 (s, 1H); 7.94 (s, 1H); 8.17 (dd, 1H); 8.85 (dd, 1H).

(2S,4S) 1-Allyloxycarbonyl-2-(allyloxycarbonylquinol-8ylcarbamoyl) pyrrolidin-4-ylthioacetate was prepared from 8-amino-6-allyloxycarbonylquinoline using a similar method to that described in example 1. (Yield: 65.3%)

NMR (DMSO-d$_6$): δ2.03–2.13 (m, 1H); 2.3 (s, 3H); 2.78–2.94 (m, 1H); 3.30–3.40 (m, 1H); 3.96–4.15 (m, 2H); 4.40–4.65 (m, 2H); 4.71–4.94 (m, 3H); 5.06–5.52 (m, 4H); 5.65–6.04 (m, 1H); 6.05–6.17 (m, 1H); 7.76 (dd, 1H); 8.47 (d, 1H); 8.68 (dd, 1H); 9.06 (s, 1H); 9.18 (s, 1H).

Preparation of the protected carbapenem:

Allyl (1R,5S6S,8R,2′S,4′S)-2-(1-allyloxycarbonyl-2-(6-allyloxycarbonylquinol-8-yl carbamoyl)pyrrolidin-4-ylthio)-6-(1-hydroxyethyl)-1-methylcarbapenem-3-carboxylate was prepared from the product of the previous step, using a similar method to that described in example 1. (Yield: 87.5%)

NMR (DMSO-d$_6$): δ1.10–1.22 (m, 6H); 2.09–2.18 (m, 1H); 2.84–2.97 (m, 1H); 3.25 (dd, 1H); 3.36–3.6 (m, 2H); 3.93–4.03 (m, 2H); 4.13–4.21 (m, 1H); 4.25 (dd, 1H); 4.3–4.36 (m, 2H); 4.5–5.5 (m, 11H); 5.55–6.02 (m, 2H); 6.03–6.17 (m, 1H); 7.72 (dd, 1H); 8.44 (d, 1H); 8.61 (dd, 1H); 9.00 (d, 1H); 9.02 (s, 1H).

EXAMPLE 3

(1R,5S,6S,8R,2′S,4′S) 2-(2.-(7-Carboxyquinol-5-ylcarbamoyl)-pyrrolidin-4-ylthio)-6-(1-hydroxyethyl)-1-methylcarbapenem-3-carboxylic Acid, Disodium Salt To a solution of allyl (1R,5S,6S,8R,2′S,4′S) 2-(2-(7-carboxyquinol-5-ylcarbamoyl)pyrrolidin-4-ylthio)-6-(1-hydroxyethyl)-1-methylcarbapenem-3-carboxylate (280 mg; 0.4 mM) in CH$_2$Cl$_2$ (4 ml) was added N,N-dimethyltrimethylsilylamine (389 μl/2.4 mM) and tetrakistriphenylphosphine palladium (46.8 mg); 0.04 mM). After stirring at ambient temperature for 15 minutes, the solvent was removed and the residue redissolved in water. After acidification to pH 4.5 with acetic acid, the solution was maintained at 0° C. for 1 hour, then basified to pH8 and extracted with CH$_2$Cl$_2$. The aqueous layer was separated and purified by subjecting to chromatography on reverse phase silica (Nucleosil C18) using a gradient of CH$_3$CN in water (0–3%), to give the title compound as a foam after freeze-drying. (65 mg; 28.5%).

NMR: δ1.11–1.21 (m, 6H); 1.82–1.90 (m, 1H); 2.65–2.76 (m, 1H); 2.81–2.95 (m, 1H); 3.18 (dd, 1H); 3.35–3.55 (m, 2H); 3.67–3.78 (m, 1H); 3.91–4.00 (m, 1H); 4.07–4.20 (m, 2H); 7.65 (dd, 1H); 8.42 (sbr, 2H); 8.99 (d, 1H). MS (+ve FAB): 571 (M+H+)

The starting material was prepared as follows:

7-Carboxy-5-nitroquinoline was prepared from 3-amino-5-nitrobenzoic acid using a similar method to that described for 8-carboxy-6-nitroquinoline in example 1. A mixture of compounds was obtained and used in the next step without separation.

7-Allyloxycarbonyl-5-nitroquinoline was prepared from the product of the previous step using a similar method to that described for 6-allyloxycarbonyl-8-nitroquinoline in example 1. (Yield: 44%)

NMR (CDCl$_3$): δ4.92–5 (m, 2H); 5.36–5.53 (m, 2H); 6.05–6.18 (m, 1H); 7.71 (dd, 1H); 9.06 (d, 1H); 9.13 (dd, 1H); 9.17 (d, 1H); 9.46 (dd, 1H).

5-Amino-7-allyloxycarbonylquinoline was prepared from 6-allyloxycarbonyl-8-nitroquinoline using a similar method to that described for 8-amino-6-allyloxycarbonylquinoline in example 1. (Yield: 24%)

NMR (CDCl$_3$): δ4.31 (s, 2H); 4.85–4.90 (m, 2H); 5.28–5.5 (m, 2H); 6.02–6.14 (m, 1H); 7.43 (d, 1H); 7.45 (dd, 1H); 8.2 (dd, 1H); 8.31 (s, 1H); 8.97 (dd, 1H).

(2S,4S) 1-Allyloxycarbonyl-2-(7-allyloxycarbonylquinol-5-ylcarbamoyl)pyrrolidin-4-yl thioacetate was prepared using a similar method to that described in example 1. (Yield: 45.6%)

NMR: δ2.05–2.15 (m, 1H); 2.35 (s, 3H); 2.81–2.97 (m, 1H); 3.32–3.43 (m, 1H); 4.00–4.13 (m, 2H); 4.53–4.71 (m, 3H); 4.85–4.97 (m, 2H); 5.07–5.55 (m, 4H); 5.84–6.01 (m, 1H); 6.05–6.20 (m, 1H); 7.68 (dd, 1H); 8.23 (s, 1H); 8.51 (s, 2H); 9.03 (dd, 1H).

Allyl (1R,5S,6S,8R,2′S,4′S)-2-(2-(7-carboxyquinol-5-ylcarbamoylpyrrolidin-4-ylthio)-6-(1-hydroxyethyl)-1-methylcarbapenem-3-carboxylate was prepared from the product of the previous step, using a similar method to that described in example 1. (Yield: 50%)

NMR: δ1.18 (d, 3H); 1.21 (d, 3H); 2.02–2.11 (m, 1H); 2.84–3.00 (m, 1H); 3.26–3.73 (m, 3H); 3.93–4.07 (m, 2H); 4.11–4.20 (m, 4.22–4.30 (m, 1H); 4.51–4.73 (m, 3H); 4.86–4.93 (m, 2H); 5.07–5.50 (m, 8H); 5.82–6.00 (m, 2H); 6.02–6.17 (m, 1H); 7.71 (dd, 1H); 8.18–8.26 (m, 1H); 8.40–8.58 (m, 1H); 8.52 (s, 1H); 9.04 (dd, 1H).

EXAMPLE 4

(1R,5S,6S,8R,2′S,4′S)-2-(3-Carboxy-2-quinolylcarbamoyl)pyrrolidine-4-ylthio)-6-(1-hydroxyethyl)-1-methylcarbapenem-3-carboxylic Acid A solution of (1R,5S,6S,8R,2′S,4′S) 2-(1-(4-nitrobenzyloxycarbonyl)-2-(3-carboxy-2-quinolylcarbamoyl)pyrrolioline-4-ylthio)-6(1-hydroxyethyl)-1-methylcarbapenem-3-carboxylic acid (dipotassium salt) (420 mg, 0.5 mmol) in water (25 ml) was hydrogenated of atmospheric pressure over Pd/carbon (10%) (300 mg) for 1 hour. The catalyst was filtered off, the filtrate note concentrated and purified by subjecting to preparatory HPLC (Nucleosil C-18), eluant water. Concentration and freeze drying gave the title compound (90 mg, 25%).

NMR: δ5 1.2 (m, 6H); 1.78 (m, 1H); 2.9 (m, 2H); 3.2 (dd, 1H); 3.4 (dq, 1H); 3.52 (m, 1H); 3.8 (m, 1H); 3.96 (dq, 1H); 4.18 (dd, 1H); 4.17 (m, 1H); 7.48 (dd, 1H); 7.72 (dd, 1H); 7.85 (d, 1H); 7.96 (d, 1H); 8.86 (s, 1H).

Ethyl 2-cyano-2-(2-nitrobenzylidine)acetate (10.5 g, 48.6 mmol) was solubilized in acetic acid (30%). The solution was cooled to 10° C. in an iced water bath. Zinc powder (6.35 g, 97 mmol) was added in small amounts to the reaction mixture, with stirring, the temperature being maintained below 15° C. After 1.5 hours the solvent was evaporated. The residue was purified by subjecting to silica gel chromatography, (eluant: ethyl acetate followed by CH2Cl2/methanol, 90/10) to give ethyl 2-amino-1-oxo-quinolin-3-carboxylate (9.6 g, quantitative).

NMR (CDCl3): δ1.47 (t, 3H); 4.47 (q, 2H); 7.25–8.0 (m, 5H); 8.45 (s, 1H); 8.55 (d, 1H).

Ethyl 2-amino-1-oxoquinoline-3-carboxylate (9.2 g, 42.5 mmol) in methanol (100 ml) was treated with a 2M aqueous solution of NaOH (45 ml, 90 mmol). The reaction mixture was stirred for 3 hours and followed by HPLC (Eluant: H2O/methanol/AcOH 1/1/0.01). At the end of the reaction, the mixture was acidified (pH3, HCl2N) and the precipitated solid filtered, washed with water, and dried under reduced pressure to give 2-amino-1-oxo-quinolin-3-carboxylic acid (7 g, 87.5%).

NMR: (DMSO-d6): δ7.20 (s, 1H); 7.60 (t, 1H); 3.72 (d, 1H); 8.05 (d, 1H); 8.20 (s, 1H).

2-Amino-1-oxo-quinoline-3-carboxylic acid (2 g, 10 mmol) in methanol (200 ml) was treated, at 0° C., with a solution of TiCl3 (15% in water), the TiCl3 solution being added drop by drop. The mixture was stirred at ambient temperature for 4 hours. Water was added to the crude mixture and the precipitate filtered, washed with water and dried to give 2-amino-quinolin-3-carboxylic acid (1.78 g, 97%).

NMR (DMSO-d6+MeOD4+NaOD/D2O): δ6.95–7.70 (M, 4M); 8.5 (S, 1H).

(2S,4S)-1-(4-Nitrobenzyloxycarbonyl)-2-(3-carboxy-2-quinolylcarbamoyl)pyrrolidin-4-ylthioacetate (2S,4S)-1-(4-Nitrobenzyloxycarbonyl)-4-acetylthio-2carboxypyrrolidine, (1.5 g, 4 mmol) was solubilized at ambient temperature in thionyl chloride (12 ml) and stirred for 5 hours. The thionyl chloride was evaporated, and the residue solubilized in CH2Cl2/toluene 1/1 (40 ml). The solvent was evaporated and dried under high vacuum for i hour. The acid chloride thus obtained was solubilized in dry CH2Cl2 (10 ml) and added, under argon, to a solution of 2-aminoquinolin-3-carboxylic acid (765 mg, 4 mmol) and diisopropylethylamine (2.12 ml, 12 mmol) in DMF (anhydrous, 20 ml), at 0° C. The mixture was stirred for 12 hours at ambient temperature, concentrated to remove the methylene chloride, and the residue subjected to chromatography on a HP20SS column, eluant MeoH/H2O/AcOH (1/100) gradient of MeoH to give the title compound (1.3 g, 60%).

NMR (DMSO d6+TFA-d): δ2.0–2.25 (m, 1H); 2.3 (s, 3H); 2.65–2.95 (m, 1H); 3.20–3.60 (m, 1H); 3..80–4.35 (m, 2H); 4.95 (m, 1H) 5.20 (s, 2H); 7.4–7.7 (m, 3H); 7.8–8.25 (m, 5H); 8.95 (s, 1H)

Allyl (1R,5R,6S,8R,2′S,4′s)-2-(1-(4-Nitrobenzyloxycarbonyl)-2-(3-Carboxy-2-quinolylcarbamoyl)pyrrolidine-4-ylthio)-6-(1-hydroxyethyl)-1-methylcarbapenem-3-carboxylate (2S,4S) 1-(4-Nitrobenzyloxycarbamoyl)-2-(3-carboxy-2-quinolylcarbamoyl)pyrrolidin-4-ylthioacetate (538 mg, 1 mmol) in methanol (25 ml) was treated with an aqueous solution of NaOH 1M (2.5 ml, 2.5 mmol) by slow addition, at 0° C. After 1 hour the mixture was acidified (pH3) with 6 HCl at 0° C., the solvent evaporated and residue dried under vacuum for 1 hour. This was disolved in DMF (2 ml) and added to a solution of allyl (1R,5R,6S,8R) 6-(1-hydroxyethyl)-1-methyl-2-diphenylphosphoryloxycarbapenem-3carboxylate (432 mg, 0.865 mmol) in DMF (5 ml), at 0° C., in the presence of diisopropylethylamine (300 ml, 1.72 mmol). The reaction mixture was stirred at ambient temperature overnight and subjected to chromatography on a HP20SS column, eluting with water/acetonitrile (gradient of acetonitrile used). The title compound (432 mg, 65%) was obtained.

1R,5R,6S,8R,2′S,4′S) 2-(1-.(4-Nitrobenzyloxycarbonyl)-2-(3-carboxy-2-quinolylcarbamoyl)pyrrolidine-4 ylthio)-6-(hydroxyethyl)-1-methylcarbapenem-3-carboxylic Acid A solution of a allyl (1R,5R,6S,8R,2′S,4′S)-2-(1-(4-nitrobenzyloxycarbonyl)-2-(3-carboxy-2-quinolylcarbamoyl)pyrrolidin4-ylthio)-6-(1-hydroxyethyl)-1-methylcarbapenem-3-carboxylate (432 mg, 0.565 mmol) in THF (20 ml) was treated at ambient temperature with triphenylphosphine (15 mg, 0.057 mmol) 0.46M potassium hexanoate in ethyl acetate (2.7 ml, 1.2 mmol) and tetrakistriphenylphosphine palladium (20 mg, 0.017 mmol) for 1 hour. Ethyl acetate (20 ml) was added to the mixture, the precipitate is filtered, washed with ethyl acetate and dried to give the title compound (420 mg, 95%).

NMR: δ1.2 (m, 6H); 1.9 (m, 1H); 3.05 (m, 1H); 3.2 (dd, 1H); 3.35 (m, 1H); 3.5 (m, 1H); 3.85–9.1 (m, 3H); 4.15 (m, 1H); 5.0–5.4 (m, 3H); 7.5 (m, 2H); 7.7 (m, 2H); 7.75–8.0 (m, 3H); 8.25 (d, 1H); 8.85 (d, 1H).

EXAMPLE 5

(1R,5S,6S,8R,2'S,4'S)-2-(2-Carboxy-4-quinolylcarbamoyl)pyrrolidin-4-ylthio)-6-(1-hydroxyethyl)-1-methylcarbapenem-3-carboxylic Acid The title compound was prepared using a similar method to that described in example 4.

NMR (DMSO-$d_6$): δ1.2 (m, 6H); 1.45 (m, 1H); 2.1 (m, 1H); 2.8 (m, 1H); 3.2 (dd, 1H); 3.4–3.6 (m, 2H); 3.7 (m, 1H); 3.9 (m, 2H); 4.15 (m, 1H); 7.6–8.2 (m, 4H); 8.9 (s, 1H,).

2-allyloxycarbonyl-4-amino-quinoline

4-Amino-2-quinoline carboxylic acid (800 mg, 4.2 mmol) in DMF (10 ml) and $K_2CO_3$ (1.17 g, 8.5 mmol) was stirred at ambient temperature in the presence of allyl bromide (1.47 ml, 17 mmol) for 24 hours. The solvent was evaporated and the crude residue purified by subjecting to silico-gel chromatography, eluting with petroleum ether ethyl acetate 1/1) to give 2-allyloxycarbonyl-4-amino-quinoline (170 mg, NMR (CDCls): δ4.75–5 (m, 4H); 5.2–5.0 (m, 2H); 5.9–6.35 (m, 1H); 7.35–8.3 (m, 5H).

(2S,4S) 1-(4-Nitrobenzyloxycarbonyl)-2-(2-allyloxycarbonyl-4-quinolylcarbamoyl) pyrrolidine-4-ylthioacetate The title compound was prepared from the product of the previous step using a similar method to that described in example 4 except using methylene chloride as the solvent.

NMR (DMSO-$d_6$): δ2.1 (m, 1H); 2.4 (s, 3H); 2.9 (m, 1H); 3.4 (m, 1H); 4.0–4.2 (m, 3H); 4.8–5.5 (m, 6H); 6.1 (m, 1H); 7.4–8.8 (m, 9H).

Allyl (1R,5S,6S,8R,2'S,4'S.) 2-(1-(4-Nitrobenzyloxycarbonyl)-2-(2-allyloxycabonyl-4-quinolylcarbamoyl) pyrrolidin-4-ylthio)-6-(1-hydroxyethyl)-1-methylcarbapenem-3-carboxylate The title compound was prepared from the product of the previous step using a similar method to that described in example 4.

NMR (DMSO-$d_6$): δ1.2 (m, 6H); 2.1 (qt, 1H); 2.9 (m, 1H); 3.3 (dd, 1H); 3.6 (m, 2H); 4.0 (m, 2H); 4.2 (m, 2H); 4.5–4.9 (m, 5H); 5.0–5.5 (m, 6H); 5.75 (m, 2H); 7.2–8.7 (m, 9H).

(1R,5S,6S,8R,2'S,4'S)-2-(1-(4-Nitrobenzyloxycarbonyl)-2-(-2-carboxy-4-quinolylcarbonyl) Pyrrolidin-4-ylthio)-6-(1-hydroxyethyl)-1-methylcarbapenem-3-carboxylic Acid The title compound was prepared from the product of the previous step using a similar method to that described in example 4.

EXAMPLE 6

(1R,5S,6S,2'S,4'S)-2-(2-(3-Carboxy-6-allyloxy-2-quinolyl-carbamoyl-pyrrolidin-4-ylthio)-6-(1-hydroxyethyl)-1-methylcarbapenem-3-carboxylic Acid A solution of (1R,5S,6S,8R,2'S,4'S) 2-(1-(4-nitrobenzyloxycarbonyl)-2-(3-carboxy-6-allyloxy-2-quinolylcarbamoyl)pyrrolidin4-ylthio)-6-(1-hydroxyethyl)-1-methylcarbapenem-3-carboxylic acid (dipotassium salt) (185 mg, 0.23 mmol) in phosphate buffer (pH 4.7), (20 ml) was treated with zinc powder (250 mg) added in small amounts to the reaction medium. The reaction was followed by HPLC. It was completed after 1 hour. The mixture was neutralized with potassium bicarbonate and the solvent evaporated. The residue was purified by subjecting to C-18 HPLC, eluting with $CH_3CN/H_2O$, to give the title compound (15 mg, 10%).

NMR: δ1.15 (m, 6H); 1.85 (m, 1H); 3.05 (m, 2H); 3.24 (dd, 1H); 3.42 (m, 1H); 3.65 (m, 1H); 3.8–4.05 (m, 2H); 4.2 (m, 1H); 4.3 (m, 1H); 4.7 (m, 1H); 5.3 (m, 1H); 5.45 (m, 1H); 6.15 (m, 1H); 7.4 (m, 2H); 7.8 (d, 1H); 8.8 (s, 1H).

Allyl-2-Amino-6-allyloxy-3-quinolylcarboxylate

2-Amino-6-hydroxy-3-quinolincarboxylic acid (600 mg, 3 mmol) in DMF (5 ml) was treated with allyl bromide (520 ml, 6 mmol) and potassium carbonate (834 mg, 6 mmol). The mixture was stirred at ambient temperature overnight, water was added and the product was extracted with methylene chloride, dried, and purified by subjecting to silica gel chromatography, (eluting with ethyl ether/petroleum ether (75/25) to give allyl-2-Amino-6-allyloxy3-quinolylcarboxylate (270 mg, 32%).

NMR (DMSO-$d_6$): δ4.6 (m, 2H); 4.85 (m, 2H); 5.22 (m, 1H); 5.3 (m, 2H); 5.5 (m, 1H); 5.85–6.35 (m, 2H); 6.95 (s, 2H); 7.4 (m, 3H); 8.7 (s, 1H).

(2S,4S)-1-(4-Nitrobenzyloxycarbonyl)-2-(3-allyloxycarbonyl-6-allyloxy-2-quinolylcarbamoyl)pyrrolidin-4-ylthioacetate (2S,4S)-1-(4-Nitrobenzyloxycarbonyl)-4-acetylthio-2-carboxypyrrolidine (325 mg, 0.88 mmol) and allyl-2-amino-6-allyloxy-3-quinolylcarboxylate (250 mg, 0.88 mmol) in $CH_2Cl_2$ (10 ml) were treated with EEDQ (240 mg, 0.97 mmol). The mixture was stirred at ambient temperature for 12 hours, the solvent evaporated, and the residue purified by subjecting to silica gel chromatography, eluting with ethyl ether to give title compound (375 mg, 67%).

NMR (DMSO-$d_6$): δ2.37 (s, 3H); 2.02 (m, 1H); 2.82 (m, 1H); 3.35 (m, 1H): 3.95–4.2 (m, 2H); 4.7 (m, 5H); 5.0–5.6 (m, 6H); 6.0–6.2 (m, 2H); 7.4–7.7 (m, 4H); 7.75–7.95 (m, 2H); 8.24 (d, 1H); 8.7 (s, 1H).

Allyl (1R,5R,6S,8R,2'S,4'S) 2-(1-(4-Nitrobenzyloxycarbonyl)-2-(3-allyloxycarbonyl-6-allyloxy-2-quinolylcarbamoyl)pyrrolidin-4-ylthio)-6-(1-hydroxyethyl)-1-methylcarbapenem-3-carboxylate The title compound was prepared using a similar method to that of example 4.

NMR (DMSO-$d_6$, AcOD-$d_4$): δ1.2 (m, 6H); 2.05 (m, 1H); 2.95 (m, 1H); 3.25 (dd, 1H); 3.4 (m, 1H); 3.6 (m, 1H); 4 (m, 1H); 4.2 (m, 2H); 4.5–4.75 (m, 6H); 5–5.5 (m, 6H); 5.85 (m, 1H); 6.1 (m, 1H); 7.45 (m, 3H); 7.65 (m, 1H); 7.8 (m, 1H); 7.9 (m, 1H); 8.2 (m, 1H); 8.8 (m, 1H).

(1R,5R,6S,8R,2'S,4'S)-2-(1-(4-Nitrobenzyloxycarbonyl)-2-(3-carboxy-6-allyloxy-2-quinolylcarbamoyl)pyrrolidin-4-ylthio)-6-(1-hydroxyethyl)-1-methylcarbapenem-3-carboxylic Acid The title compound was prepared using a similar method to that of example 4.

EXAMPLE 7

(1R,5S,6S,8R,2'S,4'S)-2-2-(2-Carboxyquinol-6-ylcarbamoyl)pyrrolidin-4-ylthio)-6-(1-hydroxyethyl)-1-methylcarbapenem-3-carboxylic Acid Disodium Salt To a solution of allyl (1R,5S,6S,8R,2'S,4'S)-2-(2-(2-carboxyquinol-6-ylcarbamoyl)pyrrolidin-4-ylthio)-6-(1-hydroxyethyl)1-methylcarbapenem-3-carboxylate (160 mg; 0.23 mM) in $CH_2Cl_2$ (12 ml) was added N,N-dimethyltrimethylsilylamine (222 µl; 0.023 mM) and tetrakistriphenylphosphine palladium (26 mg; 0.023 mM). After stirring at ambient temperature for 15 minutes, acetic acid (100 µl; 1.72 mM) and water (2 ml) were added. The mixture was stirred for 15 minutes, then basified to pH8. The aqueous layer was separated and purified by subjecting to chromatography on reverse phase silica (Nucleosil C18) using a gradient of $CH_3CN$ in water (0–15%) to give the title compound as a foam after freeze-drying (38 mg; 29%).

NMR δ:1.10–1.20 (m, 6H); 1.70–1.85 (m, 1H); 2.60–2.70 (m, 1H); 2.82 (dd, 1H); 3.20 (dd, 1H); 3.35–3.48 (m, 2H); 3.62–3.72 (m, 1H); 3.90–4.03 (m, 2H); 4.10–4.20 (m, 1H); 7.90–8.50 (m, 5H). MS (+ve FAB): 525 (M-H).

The starting material was prepared as follows:

To a solution of 2-benzylidene-6-nitroquinoline (4.9 g; 17.7 mM) in pyridine (36.6 ml) and water (8 ml) was added portion wise $KMnO_4$ (7.5 g; 47.8 mM) keeping the temperature between 18 and 20° C. After filtration on celite, the solution was acidified (pH3), at 0° C., with $H_2SO_4$ (65%). The resulting precipitate was filtered, washed with water and ether and then dried to give 2-carboxy-6-nitroquinoline (1.5 g; 39%).

NMR (DMSO-$d_6$+$CF_3COOD$): δ8.26 (d, 1H); 8.36 (d, 1H); 8.54 (dd, 1H); 8.90 (d, 1H); 9,17 (d, 1H). MS (CI+): 219 (M+H).

To a solution of 2-carboxy-6-nitroquinoline (1.5 g; 6.8 mM) in THF (30 ml) was added triphenylphosphine (2.7 g; 10.2 mM), allyl alcohol (0.7 ml; 10.2 mM) and DEAD (1.63 ml; 10.2 mM). After stirring at ambient temperature for 30 minutes, the mixture was extracted with ethyl acetate and purified by subjecting to flash chromatography, eluting with ethyl acetate/petroleum ether (40/60) to give 2-allyloxycarbonyl-6-nitroquinoline (1.2 g; 71%).

NMR (CDCCl$_3$): δ5.0–5.03 (m, 2H); 5.35–5.55 (m, 2H); 6.07–6.20 (m, 1H); 8.34 (d, 1H); 8.47 (d, 1H); 8.52–8.59 (m, 2H); 8.86 (d, 1H).

To a solution of 2-allyloxycarbonyl-6-nitroquinoline (1.25 g; 4.8 mM) in MeOH (20 ml) was added $SnCl_2.2H_2O$ (7.65 g; 33.6 mM). After stirring at ambient temperature for 3 hours, the mixture was evaporated to dryness and the residue partitioned between an aqueous solution of $NH_4OH$ (pH 8.5) and ethyl acetate. The organic phase was concentrated and purified by subjecting to flash chromatography, eluting with ethyl acetate/petroleum ether (65/35) to give 2-allyloxycarbonyl-6-aminoquinoline (280 mg; 28%).

NMR (CDCl$_3$): δ4.93–5.00 (m, 2H); 5.28–5.50 (m, 2H); 6.05–6.18 (m, 1H); 6.90 (d, 1H); 7.20 (dd, 1H); 7.90 (d, 1H); 8.04–8.13 (m, 9H).

To a solution of (2S,4S)-1-allyloxycarbonyl-2-carboxypyrrolidin-4-ylthioacetate (360 mg, 1.3 mM) in $CH_2Cl_2$ (15 ml) was added $SOCl_2$ (865 µl; 13 mM). After stirring at ambient temperature for 3 hours, the solvent was evaporated and dried under reduced pressure. The product was dissolved in $CH_2Cl_2$ (25 ml) and the resulting solution added dropwise to a solution of 2-allyloxycarbonyl-6-aminoquinoline (270 mg; 1.18 mM) and N-ethyl diisopropylamine (432 µl; 2.47 mM) in $CH_2Cl_2$ (10 ml).

After stirring at ambient temperature for 2 hours, the mixture was partitioned between HCl(1N) and $CH_2Cl_2$. The organic phase was concentrated and purified by subjecting to flash chromatography, eluting with ethyl acetate/petroleum ether (65/35), to give (2S,4S)-1-allyloxycarbonyl-2-(2-allyloxycarbonylquinol-6-ylcarbamoyl-pyrrolidin-4-ylthioacetate (420 mg; 66%).

NMR (DMSO-$d_6$+$CF_3COOD$): δ1.88–2.03 (m, 1H); 2.34 (s, 3H); 2.77–2.92 (m, 1H); 3.96–4.12 (m, 2H); 4.43–4.63 (m, 3H); 4.86–5.30 (m, 5.72–6.17 (m, 2H); 7.97 (d, 1H); 8.12 (d, 1H); 8.18 (d, 1H); 8.45–8.56 (m, 2H). MS: (+ve FAB): 484 (M+H).

Preparation of the protected carbapenem.

To a solution of the above thioacetate (410 mg; 0.84 mM) in ethanol (5 ml) was added, at 0° C., a solution of methylamine in ethanol (5M) (1.02 ml; 5.04 mM). After stirring at ambient temperature for 2 hours, the solvent was removed by evaporation and the resulting thiol dried under vacuum, dissolved in DMF (4 ml) and added to a solution of allyl (1R,5R,6S,8R)-6-(1-hydroxyethyl)-1-methyl-2-diphenylphosphoryloxycarbapenem-3-carboxylate (420 mg; 0.84 mM), tri-n-butylphosphine (2.09 µl; 0.84 mM), N-ethyl diisopropylamine (292 µl; 1.68 mM) and water (15 µl; 0.84 mM) in DMF (10 ml). The mixture was stirred at ambient temperature for 2 hours. After evaporation of the solvent, the residue was extracted with ethyl acetate and purified by subjecting to flash chromatography, eluting with ethyl acetate/$CH_3CN$ (95/5) to give allyl (1R,5S,6S,8R,2'S,4'S)-(2-(1-allyloxycarbonyl-2-(2-allyloxycarbonylquinol-6-ylcarbamoyl)pyrrolidin-4-ylthio)-6-(1-hydroxyethyl)-1-methylcarbapenem-3-carboxylate as a foam (160 mg; 27.5%).

NMR (DMSO-$d_6$): δ1.1–1.2 (dd, 6H); 1.8–2.0 (m, 1H); 2.75–2.90 (m, 1H); 3.25–3.40 (m, 2H); 3.50–3.60 (m, 1H); 3.90–5.50 (m, 17H); 5.70–6.15 (m, 3H); 7.85–8.50 (m, 5H). MS (+ve FAB): 691 (M+H).

EXAMPLE 8

(1R,5S,6S,8R,2'S,4'S)-2-(2-(4-Carboxyquinol-8-ylcarbamoyl)pyrrolidin-4-ylthio)-6-(1-hydroxyethyl)-1-methylcarbapenem-3-carboxylic Acid Disodium Salt The title compound was prepared from the allyl protected compound using a similar method to that described in example 7 (Yield: 30%).

NMR (DMSO+$CD_3COOD$): δ1.08–1.11 (m, 6H); 1.75–1.87 (m, 1H); 2.63–2.75 (m, 1H); 3.20 (dd, 1H); 3.38–3.50 (m, 1H); 3.51–3.65 (m, 2H); 3.90–4.00 (m, 1H); 4.03–4.12 (m, 2H); 4.17 (dd, 1H); 7.56 (t, 1H); 7.71 (d, 1H); 8.27 (d, 1H); 8.71 (d, 1H); 8.90 (d, 1H).

The starting material was prepared as follows:

To a suspension of 4-carboxyquinoline (5 g; 28.9 mM) in concentrated sulphuric acid (10 ml) was added, at 65° C., fuming nitric acid (9 ml) and concentrated sulphuric acid (9 ml). After stirring at 75° C for 30 minutes, the mixture was poured onto ice; the pH adjusted to pH3 and the resulting precipitate filtered and dried to give a mixture of 4-carboxy-8-nitroquinoline and 4-carboxy-5-nitroquinoline which was not separated (4.4 g; 70%).

NMR (DMSO-$d_6$): 8 7.97–8.03 (m, 2H); 8.37 (d, 1H); 8.47 (d, ! H); 9.19 (d, 1H).

The above mixture was treated using a similar method to that described for the preparation 2-allyloxycarbonyl-6-nitroquinoline in example 4, to give a mixture of 4-allyloxycarbonyl-8-nitroquinoline (Yield: 23%) and 4-allyloxycarbonyl-5-nitroquinoline (Yield: 72%) which was separated by flash chromatography, eluting with ethyl acetate/petroleum ether (40/60).

NMR (DMSO-$d_6$): $\delta$4.93–5.00 (m, 2H); 5.32–5.53 (m, 2H); 6.06–6.17 (m, 1H); 7.92 (dd, 1H); 8.17 (d, 1H); 8.37 (dd, 1H); 8.88 (dd, 1H); 9.20 (d, 1H).

4-Allyloxy-8-aminocarbonylquinoline was prepared from 4-allyloxycarbonyl-8-nitroquinoline using a similar method to that described for the preparation of 2-allyloxy-6-aminocarbonylquinoline in example 7. (Yield: 92%; mp: 44–46%).

NMR (DMSO-$d_6$+CF$_3$COOD): $\delta$4.94–5.00 (m, 2H); 5.32–5.53 (m, 2H); 6.05–6.20 (m, 1H); 7.61 ({t, 1H); 7.71 (t, 1H); 8.09 (d, 1H); 8.34 (d, 1H); 9.12 (d, 1H). MS: (CI+): 229 (H+H).

The side-chain pyrrolidin-4-yl-thioacetate, (2S,4S)-1-allyloxycarbonyl-2-(4-allyloxycarbonylquinol-8-ylcarbamoyl)pyrrolidin4-ylthioacetate, was prepared from 4-allyloxycarbonyl-8-aminoquinoline using a similar method to that described in example 7. (Yield: 50%).

NMR (DMSO+CD$_3$COOD): $\delta$2.04–2.15 (m, 1H); 2.29 (s, 3H); 2.77–2.95 (m, 1H); 3.30–3.46 (m, 1H); 3.94–4.17 (m, 2H); 4.40–5.52 (m, 9H); 5.63–6.20 (m, 2H); 7.73 (t, 1H); 8.07 (d, 1H); 8.29 (d, 1H); 8.65–8.75 (m, 1H); 9.07 (d, 1n). MS: (+ve FAB): 484 (H+H).

Preparation of the protected carbapenem:

Allyl (1R,5S,6S,8R,2'S,4'S)-2-(1-allyloxycarbonyl-2-(4-allyloxycarbonylquinol-8-ylcarbamoyl)pyrrolidin-4-ylthio)-6-(1-hydroxyethyl)-1-methylcarbapenem-3-carboxylate was prepared from the product of the previous step, using a similar method to that described in example 7 (Yield: 30%).

NMR (DMSO-$d_6$+CD$_3$COOD): $\delta$1.08–1.24 (m, 6H); 2.02–2.15 (m, 2.82–2.97 (m, 1H); 3.23 (dd, 1H); 3.47–3.57 (m, 2H); 3.82–4.05 (m, 2H); 4.10–4.30 (m, 2H); 4.47–5.50 (m, 13H); 5.62–6.18 (m, 3H); 7.73 (t, 8.05 (d, 1H); 8.27 (d, 1H); 8.65–8.75 (m, 1H); 8.97–9.10 (m, 1H). MS: (+ve FAB): 691 (H+H).

EXAMPLE 9

(1R,5S,6S,8R,2'S,4'S)-2-(2-(4-Carboxyquinol-ylcarbamoyl)pyrrolidin-4-ylthio)-6-(1-hydroxyethyl)-1-methylcarbapenem-3-carboxylic Acid Disodium Salt The title compound was prepared from the allyl protected compound using a similar method to that described in example 7 ., (Yield: 24%).

NMR (DMSO-$d_6$+CD$_3$COOD): $\delta$1.13–1.22 (m, 6H); 1.85–1.95 (m, 1H); 2.83–2.95 (m, 1H); 3.03–3.12 (m, 1H); 3.20–3.25 (m, 1H); 3.38–3.47 (m, 1H); 3.57–3.68 (m, 1H); 3.81–4.03 (m, 2H); 4.16–4.30 (m, 2H); 7.49 (d, 1H); 7.73 (t, 1H); 7.88 (d, 1H); 8.00 (d, 1H); 8.82 (d, 1H).

The starting material was prepared as follows:

4-Allyloxycarbonyl-5-nitroquinoline was prepared from 4-carboxy-5-nitroquinoline using a similar method to that described in example 8 (Yield: 72%).

NMR (DMSO-$d_6$): $\delta$4.74–4.81 (m, 2H); 5.28–5.47 (m, 2H); 5.93–6.07 (m, 1H); 8.0–8.07 (m, 1H); 8.42 (d, 1H); 8.59 (d, 1H); 9.23 (d, 1H). MS (CI+): 259 (M+H).

4-Allyloxycarbonyl-5-aminoquinoline was prepared from the product of the previous step, using a similar method to that described in example 7 (Yield: 28%).

NMR (DMSO-$d_6$): $\delta$4.91–4.98 (m, 2H); 5.30–5.52 (m, 2H); 6.03–6.15 (m, 1H); 7.02 (d, 1H); 7.42–7.45 (m, 2H); 7.56 (t, 1H); 8.88 (d, 1H).

Preparation of the side-chain pyrrolidin-4-ylthioacetate:

(2S,4S) 1-Allyloxycarbonyl-2-(4-allyloxycarbonylquinol-5-ylcarbamoyl)pyrrolidin-4-yl thioacetate was prepared using a similar method to that described in example 7 (Yield: 53%).

NMR (DMSO-$d_6$+CD$_3$COOD): $\delta$1.95–2.12 (m, 1H); 2.35 (s, 3H); 2.68–2.88 (m, 1H); 3.17–3.33 (m, 1H); 3.90–4.10 (m, 2H); 4.43–5.48 (m, 9H); 5.84–6.15 (m, 2H); 7.50–7.62 (m, 1H); 7.63–7.70 (m, 1H); 7.83–7.97 (m, 1n); 8.08 (d, 1H); 9.05 (d, 1H). MS: (+ve FAB): 484 (M+H).

Preparation of the protected carbapenem:

Allyl (1R,5S,6S,8R,2'S,4'S)-2-(1-allyloxycarbonyl-2-(4-allyloxycarbonylquinol-5-ylcarbamoyl)pyrrolidin-4-ylthio)-6-(1-hydroxyethyl)-1-methylcarbapenem-3-carboxylate was prepared from the product of the previous step, using a similar method to that described in example 7 (Yield: 25%).

NMR (DMSO-$d_6$+CD$_3$COOD): $\delta$1.11–1.23 (m, 6H); 1.95–2.10 (m, 1H); 2.72–2.90 (m, 1H); 3.27 (dd, 1H); 3.35–3.62 (m, 2H), 3.88–4.05 (m, 2H); 4.10–4.30 (m, 2H); 4.40–5.47 (m, 13H); 5.80–6.15 (m, 3H); 7.52–7.68 (m, 2H); 7.71–7.90 (m, 1H); 8.05–8.13 (m, 1H); 8.96–9.03 (m, 1H). MS (+ve FAB): 691 (M+H).

EXAMPLE 10

(1R,5S,6S,8R,2'S,4'S)-2-(2-(2-Carboxyquinol-8-ylcarbamoyl)pyrrolidin-4-ylthio)-6-(1-hydroxyethyl)-1-methylcarbapenem-3-carboxylic Acid Disodium Salt The title compound was prepared from the allyl protected compound using a method similar to that described in example 7 (Yield: 19%).

NMR (DMSO-$d_6$+CD$_3$COOD): $\delta$1.06–1.11 (m, 6H); 1.78–1.88 (m, 1H); 2.64–2.77 (m, 2H); 3.20 (dd, 1H); 3.40–3.68 (m, 3H); 3.90–4.00 (m, 1H); 4.10–4.20 (m, 2H); 7.65–7.77 (m, 2H); 8.18 (d, 1H); 8.53 (d, 1H); 8.73 (d, 1H).

The starting material was prepared as follows:

To a solution of 2-carboxyquinoline (5 g, 29 mM) in concentrated H$_2$SO$_4$ (15 ml) was added a mixture of fuming HNO$_3$ (5 ml) and concentrated H$_2$SO$_4$ (10 ml). After stirring at ambient temperature for 30 minutes, the pH of the mixture was brought to pH 3.5 with a 50% aqueous solution of NaOH. The resulting solid was filtered and dried to give a mixture of 2-carboxy-8-nitroquinoline and 2-carboxy-5-nitroquinoline which was used in the next step (5 g, 79%).

NMR (DMSO-$d_6$+CF$_3$COOD): $\delta$7.89 (t, 1H); 8.28 (d, 1H); 8.34–8.43 (m, 2H); 8.77 (d, 1H).

The above mixture was treated with allyl alcohol using a similar method to that described for the preparation of 2-allyloxycarbonyl-6-nitroquinoline to give, after chromatography, 2-allyloxycarbonyl-8-nitroquinoline (Yield: 30%) and 2-allyloxycarbonyl-5-nitroquinoline (Yield: 50%).

2-allyloxycarbonyl-8-nitroquinoline:

NMR (DMSO-$d_6$): $\delta$4.90–5.00 (m, 2H); 5.30–5.55 (m, 2H); 6.05–6.19 (m, 1H); 7.91 (t, 1H); 8.30 (d, 1H); 8.40–8.43 (m, 2H); 8.80 (d, 1H). MS: (CI+): 259 (M+H).

2-Allyloxycarbonyl-8-aminoquinoline was prepared by reducing the product of the previous step, using a similar method to that described in example 7 (Yield: 88%).

NMR (DMSO-d$_6$): δ4.88–4.93 (m, 2H); 5.30–5.50 (m, 2H); 6.05–6.17 (m, 1H); 6.94 (d, 1H); 7.15 (d, 1H); 7.43 (t, 1H); 8.04 (d, 1H); 8.35 (d, 1H).

Preparation of the side-chain pyrrolidin-4-ylthioacetate:

(2S,4S) 1-Allyloxycarbonyl-2-(2-allyloxycarbonyl-quinol-8-ylcarbamoyl)pyrrolidin-4-ylthioacetate was prepared from the product of the previous step using a similar method to that described in example 7 (Yield: 80%).

NMR (DMSO-d$_6$): δ2.05–2.19 (m, 1H); 2.22 (s, 3H); 2.82–2.95 (m, 1H); 3.30–3.60 (m, 1H); 4.00–4.20 (m, 2H); 4.40–5.50 (m, 9H); 5.60–6.20 (m, 2H); 7.70–7.85 (m, 2H); 8.22 (d, 1H); 8.60–8.70 (m, 2H). MS (+ve) FAB: 484 (M+H).

Preparation of the protected carbapenem:

Allyl (1R,5S,6S,8R,2'S,4'S)-2-(1-allyloxycarbonyl-2-(2-allyloxycarbonylquinol-8-ylcarbamoyl)pyrrolidin-4-ylthio)-6-(1-hydroxyethyl)-1-methylcarbapenem-3-carboxylate was prepared from the product of the previous step, using a similar method to that described in example 7 (Yield:

NMR (DMSO-d$_6$+CD$_3$COOD): δ1.12–1.24 (m, 6H); 2.10–2.20 (m, 1H); 2.89–3.02 (m, 1H); 3.25 (dd, 1H); 3.45–3.55 (m, 1H); 3.62–3.73 (m, 1H); 3.96–4.28 (m, 4H); 4.48–5.52 (m, 13H); 5.58–6.23 (m, 3H); 7.68–7.80 (m, 2H); 8.18 (d, 1H); 8.58 (d, 1H); 8.67 (d, 1H). MS (+ve) FAB: 691 (M+H).

EXAMPLE 11

(1R,5S,6S,8R,2'S,4'S)-2-(2-(2-Carboxyquinol-5-ylcarbamoyl)pyrrolidin-4-ylthio)-6-(1-hydroxyethyl)-1-methylcarbapenem-3-carboxylic Acid Disodium Salt The title compound was prepared from the allyl protected compound using a similar method to that described in example 7 (Yield: 33%).

NMR (DMSO-d$_6$+CD$_3$COOD): δ1.13–1.23 (m, 6H); 1.83–1.92 (m, 1H); 2.67–2.77 (m, 1H); 2.85–2.95 (m, 1H); 3.22 (dd, 1H); 3.40–3.57 (m, 2H); 3.68–3.78 (m, 1H); 3.93–4.03 (m, 1H); 4.05–4.21 (m, 2H), 7.84 (t, 1H); 7.94–8.05 (m, 2H); 8.25 (d, 1H); 8.51 (d, 1H).

The starting material was prepared as follows:

2-Allyloxycarbonyl-5-nitroquinoline was obtained as described in example 10 (Yield: 50%).

NMR (DMSO-d$_6$): δ4.90–5.00 (m, 2H); 5.30–5..55 (m, 2H); 6.05–6.19 (m, 1H); 8.06 (t, 1H); 8.36 (d, 1H); 8.55–8.63 (m, 2H); 9.05 (d, 1H). MS (CI+): 259 (M+H).

2-Allyloxycarbonyl-5-aminoquinoline was prepared by reducing the product of the previous step, using a similar method to that described in example 7 (Yield: 65%).

NMR (DMSO-d$_6$): δ4.83–4.93 (m, 2H); 5.28–5.50 (m, 2H); 6.03–6.15 (m, 1H); 6.82 (d, 1H); 7.31 (d, 1H); 7.53 (t, 1H); 7.95 (d, 1H); 8.71 (d, 1H). MS: (CI+): 229 (M+H).

Preparation of the side-chain pyrrolidin-4-ylthioacetate:

(2S,4S) 1-Allyloxycarbonyl-2-(2-allyloxycarbonyl-quinol-5 -ylcarbamoyl)pyrrolidin-4-ylthioacetate was prepared using a similar method to that described in example 7 (Yield:

NMR (DMSO-d$_6$+CD$_3$COOD): δ1.98–2.13 (m, 1H); 2.35 (s, 3H); 2.80–2.98 (m, 1H); 3.27–3.43 (m, 1H); 3.96–4.11 (m, 2H); 4.50–4.68 (m, 3H); 4.86–5.52 (m, 6H); 5.84–6.20 (m, 2H); 7.73–7.92 (m, 2H); 8.05 (d, 1H); 8.16 (d, 1H); 8.50–8.72 (m, 1H). MS (+ve FAB): 484 (M+H).

Preparation of the protected carbapenem:

Allyl (1R,5S,6S,8R,2'S,4'S)-2-(1-allyloxycarbonyl-2-(2-allyloxycarbonylquinol-5-ylcarbamoyl)pyrrolidin-4-ylthio)-6-(1-hydroxyethyl)-1-methylcarbapenem-3-carboxylate was prepared from the product of the previous step, using a similar method to that described in example 7 (Yield: 63%).

NMR: (DMSO-d$_6$+CD$_3$COOD): δ1.17–1.24 (m, 6H); 2.00–2.14 (m, 1H); 2.82–3.00 (m, 1H); 3.28 (dd, 1H); 3.32–3.62 (m, 2H); 3.94–4.09 (m, 2H); 4.12–4.30 (m, 2H); 4.53–5.52 (m, 13H); 5.83–6.20 (m, 3H); 7.76–7.92 (m, 2H); 8.08 (d, 1H); 8.18 (d, 1H); 8.52–8.71 (m, 1H). MS (+ve FAB): 691 (M+H).

EXAMPLE 12

(1R,5S,6S,8R,2'S,4'S)-2-(2-(4-Carboxyquinol-2-ylcarbamoyl)pyrrolidin-4-ylthio)-6-(1-hydroxyethyl)-1-methylcarbapenem-3-carboxylic Acid Disodium Salt The title compound was prepared from the allyl protected compound using a similar method to that described in example 7 (Yield: 28%).

NMR (DMSO-d$_6$+CD$_3$COOD): δ1.10–1.21 (m, 6H); 1.80–1.88 (m, 1H); 2.65–2.86 (m, 2H); 3.20 (dd, 1H); 3.35–3.55 (m, 2H); 3.62–3.76 (m, 1H); 3.90–4.01 (m, 1H); 4.05–4.20 (m, 2H); 7.52 (t, 1H); 7.62 (t, 1H); 7.86 (d, 1H); 8.51–8.62 (m, 2H). MS: (ES+): 527 (M+H).

Preparation of the side-chain pyrrolidin-4-ylthioacetate:

To a solution of (2S,4S)-1-allyloxycarbonyl-2-carboxy-pyrrolidin-4-yl thioacetate (1.45 g, 5.3 mM) in CH$_2$Cl$_2$ (15 ml) was added SOCl$_2$ (5 ml, 68.5 mM). After stirring at ambient temperature for 3 hours, the solvent was evaporated and dried under reduced pressure. The product was dissolved in CH$_2$Cl$_2$ (25 ml) and the resulting solution added dropwise to a solution of 2-amino-4-carboxyquinoline (1 g; 5.3 mM), N-ethyl diisopropylamine (4.5 ml, 26.5 mM) and trimethylethylchloride (2.2 ml, 17.8 mM). The mixture was stirred at ambient temperature overnight. After extraction with methylene chloride, the material was used in the next step without further purification.

NMR (DMSO-d$_6$+CD$_3$COOD): δ1.85–2.00 (m, 1H); 2.30 (s, 3H); 2.68–2.90 (m, 1H); 3.23–3.47 (m, 1H); 3.86–4.05 (m, 2H); 4.40–4.58 (m, 5.04–5.37 (m, 2H); 5.69–6.00 (m, 1H); 7.60 (t, 1H); 7.77 (t, 1H); 7.88 (d, 1H); 8.60 (d, 1H); 8.68–8.80 (m, 1H).

(2S,4S)-1-Allyloxycarbonyl-2-(2-carboxyquinol-4-yl carbamoyl)pyrrolidin-4-ylthioacetate was converted to (2S,4S)-1-allyloxycarbonyl-2-(2-allyloxycarbonyl-quinol-4-ylcarbamoyl)pyrrolidin-4-ylthioacetate using a similar method to that used in the protecting step described for preparation of 2-allyloxycarbonyl-6-nitroquinoline in example 7 (Yield: 57%).

NMR (DMSO-d$_6$+CD$_3$COOD); δ1.85–2.03 (m, 1H); 2.35 (s, 3H); 2.72–2.90 (m, 1H); 3.12–3.38 (m, 1H); 3.90–4.11 (m, 2H); 4.41–4.74 (m, 3H); 4.88–5.50 (m, 6H); 5.70–6.20 (m, 2H); 7.63 (t, 1H); 7.82 (t, 1H); 7.94 (d, 1H); 8.55 (d, 1H); 8.73–8.87 (m, 1H). MS (+ve FAB): 484 (M+H).

Preparation of the protected carbapenem:

Allyl (1R,5S,6S,8R,2'S,4'S)-2-(1-allyloxycarbonyl-2-(4-allyloxycarbonylquinol-2-ylcarbamoyl)pyrrolidin-4-ylthio)-6-(1-hydroxyethyl)-1-methylcarbapenem-3-carboxylate was prepared from the product of the previous step, using a similar method to that described in example 7 (Yield: 75%).

NMR (DMSO-$d_6$+CD$_3$COOD): $\delta$1.10–1.22 (m, 6H); 1.85–1.98 (m, 1H); 2.76–2.92 (m, 1H); 3.25–3.37 (m, 2H); 3.48–3.62 (m, 1H); 3.90–4.06 (m, H); 4.10–4.28 (m, 2H); 4.40–5.50 (m, 13H); 5.70–6.18 (m, 3H); 7.64 (t, 1H); 7.82 (t, 1H); 7.94 (d, 1H); 8.55 (d, 1H); 8.76–8.86 (m, 1H). MS (+ve FAB): 691 (M+H).

EXAMPLE 13

(1R,5S,6S,8R,2'S,4'S)-2-(2-(7-Carboxy-2,3-dimethylquinoxalin-5-ylcarbamoyl)pyrrolidin-4-ylthio)-6-(1-hydroxyethyl)-1-methylcarbapenem-3-carboxylic Acid Disodium Salt The title compound was prepared from the allyl protected compound using a similar method to that described in example 7 (Yield: 18%).

NMR (DMSO-$d_6$+CD$_3$COOD): $\delta$1.00–1.10 (m, 6H); 1.70–1.85 (m, 1H); 2.59–2.69 (m, 8H); 3.10 (dd, 1H); 2.28–3.40 (m, 1H); 3.45–3.58 (m, 2H); 3.81–3.92 (m, 1H); 3.97–4.03 ), (m, 1H); 4.08 (dd, 1H); 8.10 (s, 1H); 9.00 (s, 1H). MS (−ve FAB): 554 (M−H).

The starting material was prepared as follows:

To a solution of 4-amino-3,5-dinitrobenzoic acid (2 g; 8.8 mM) in THF (30 ml) was added triphenylphosphine (3 g; 11.44 mM) allyl alcohol (778 μl; 11.44 mM) and DEAD (18 ml; 11.44 mM).

After stirring at ambient temperature for 30 minutes, the mixture was extracted with ethyl acetate and purified by subjecting to flash chromatography, eluting with CH$_2$Cl$_2$, to give allyl 4-amino-3,5-dinitrobenzoate (Yield: 100%).

NMR (DMSO-$d_6$): $\delta$5.81 (m, 2H); 5.20–5.46 (m, 2H); 6.00–6.17 (m, 1H); 8.66–8.86 (m, 4H).

To a suspension of the above compound (1.5 g; 5.6 mM) in EtOH (20 ml) was added a solution of ammonium sulphide (20%, 18 ml). After heating at reflux for 30 minutes, the mixture was evaporated to dryness and the residue taken up with water. The resulting solid was treated with MeOH and the insoluble material removed by filtration. After evaporation to dryness, allyl 3,4-diamino-5-nitrobenzoate was obtained as a solid (850 mg; 64%).

NMR (DMSO-$d_6$): $\delta$4.73–4.78 (m, 2H); 5.23–5.42 (m, 2H); 5.97–6.18 (m, 1H); 7.32 (d, 1H); 8.02 (d, 1H). MS (CI+): 238 (M+H).

A solution of the above compound (0.5 g; 2.1 mM) and biacetyl (0.258 ml; 2.94 mM) in ethanol (25 ml) was heated at reflux for 7 hours. After filtration of the insoluble material, the compound was purified by flash chromatography, eluting with CH$_2$Cl$_2$, to give 7-allyloxycarbonyl-2,3-dimethyl-5-nitroquinoxaline (348 mg; 58%). NMR (CDCl$_3$): $\delta$2.77–2.85 (m, 6H); 4.90–4.95 (m, 2H); 5.33–5.50 (m, 2H); 6.00–6.13 (m, 1H); 8.59 (d, 1H); 8.90 (d, 1H). MS (CI+): 288 (M+H).

7-Allyloxycarbonyl-5-amino-2,3-dimethylquinoxaline was prepared from the above compound using a similar method to that described for the preparation of 6-amino-2-allyloxycarbonylquinoline in example 7 (Yield: 100%).

NMR (CDCl$_3$): $\delta$2.68–2.77 (m, 6H); 4.80–4.90 (m, 2H), 5.25–5.50 (m, 2H); 6.00–6.13 (m, 1H); 7.46 (d, 1H); 8.07 (d, 1H). MS (CI+): 258 (M+H).

Preparation of the side-chain pyrrolidin-4-ylthioacetate:

(2S,4S) 1-Allyloxycarbonyl-2-(7-allyloxycarbonyl-2,3-dimethylquinoxalin-5-ylcarbamoylpyrrolidin-4-ylthioacetate was prepared using a similar method to that described in example 7 (Yield: 80%).

NMR (DMSO-$d_6$+CF$_3$COOD): $\delta$2.03–2.20 (m, 1H); 2.30–2.95 (m, 1H); 2.75 (s, 3H); 2.79 (s, 3H); 3.33 (m, 1H); 4.00–4.17 (m, 2H); 4.45–5.50 (m, 9H); 5.65–6.18 (m, 2H); 8.26 (d, 1H); 9.00–9.15 (m, 1H). MS (+ve FAB): 513 (M+H).

Preparation of the protected carbapenem:

Allyl (1R,5S,6S,8R,2'S,4'S)-2-(1-allyloxycarbonyl-2-(7-allyloxycarbonyl-2,3-dimethylquinoxalin-5-ylcarbamoyl)pyrrolidin-4-ylthio)-6-(1-hydroxyethyl)-1-methylcarbapenem-3-carboxylate was prepared from the product of the previous step, using a similar method to that described in example 7 (Yield: 20%).

NMR (DMSO-$d_6$+CD$_3$COOD): $\delta$1.08–1.25 (m, 6H); 2.07–2.20 (m, 1H); 2.63–2.80 (m, 6H); 2.80–3.00 (m, 1H); 3.25 (dd, 1H); 3.50 (m, 2H); 3.90–4.30 (m, 5H); 4.40–5.50 (m, 12H); 5.60–6.20 (m, 3H); 8.27 (s, 1H); 9.00–9.13 (m, 1H). MS (+ve FAB): 720 (M+H).

EXAMPLE 14

(1R,5S,6S,8R,2'S,4'S)-2-(2-(4-Carboxyquinazolin-2-ylcarbamoyl)-pyrrolidin-4-ylthio)-6-(1-hydroxyethyl)-1-methylcarbapenem-3-carboxylic Acid Disodium Salt The title compound was prepared from the allyl protected compound using a similar method to that described in example 7 (Yield: 15%).

NMR: (DMSO-$d_6$+CD$_3$C00D): $\delta$1.05–1.25 (m, 6H); 1.70–1.80 (m, 1H); 2.60–2.85 (m, 2H); 3.15 (dd, 1H); 3.25–3.50 (m, 2H); 3.55–3.70 (m, 1H); 3.90–4.00 (m, 1H); 4.00–4..20 (m, 2H); 7.50 (m, 1H); 7.75 (d, 1H); 7.85 (m, 1H); 8.48 (d, 1H). MS −ve FAB: 526 (M−H).

The starting material was prepared as follows:

4-Allyloxycarbonyl-2-aminoquinazoline was prepared from 2-amino-4-carboxyquinazoline using a similar method to that used in the protecting step described in example 7 (Yield: 42%).

NMR (DMSO-$d_6$): $\delta$4.91–4.98 (m, 2H); 5.33–5.49 (m, 2H); 6.03–6.13 (m, 1H); 7.16–7.30 (m, 1H); 7.50 (d, 1H); 7.60 (m, 1H); 7.90 (d, 1H).

Preparation of the side-chain pyrrolidin-4-ylthioacetate:

(2S,4S)-1-Allyloxycarbonyl-2-(4-allyloxycarbonylquinazolin-2-ylcarbamoyl)pyrrolidin-4-ylthioacetate was prepared using a method to that described in example 7.

NMR (DMSO-$d_6$): $\delta$1.90–2.00 (m, 1H); 2.33 (s, 3H); 2.80–3.00 (m, 1H); 3.20–3.45 (m, 1H); 3.90–4.15 (m, 2H); 4.40–4.55 (m, 1H); 4.90–5.55 ( 8H); 5.80–6.95 (m, 2H); 7.20–8.40 (m, 4H).

Preparation of the protected carbapenem:

Allyl (1R,5S,6S,8R,2'S,4'S)-2-(1-allyloxycarbonyl-2-(4-allyloxycarbonylquinazolin-2-ylcarbamoyl)pyrrolidin-4-ylthio)-6-(1-hydroxyethyl)-1-methylcarbapenem-3-carboxylate was prepared from the product of the previous step, using a similar method to that described in example 7 (Yield: 23%).

NMR (DMSO-$d_6$+CD$_3$COOD): $\delta$1.08–1.25 (m, 6H); 1.80–2.00 (m, 1H); 2.80–3.05 (m, 1H); 3.20–3.70 (m, 3H); 3.85–4.30 (m, 4H); 4.40–5.55 (m, 13H); 5.70–6.20 (m, 3H); 7.70 (m, 1H); 7.90–8.15 (m, 2H); 8.30 (d, 1H). MS (v+e FAB): 692 (M+H).

EXAMPLE 15

(1R,5S,6S,8R,2'S,4'S)-2-(2-(3-Carboxyisoquinol-5-ylcarbamoyl)-pyrrolidin-4-ylthio)-6-(1-hydroxyethyl)-1-methylcarbapenem-3-carboxylic Acid Disodium Salt The title compound was prepared from the allyl protected compound using a similar method to that described in example 7 (Yield: 30%).

NMR (DMSO-$d_6$+CD$_3$COOD): δ1.14–1.23 (m, 6H); 1.82–1.94 (m, 1H); 2.68–2.80 (m, 1H); 2.82–2.92 (m, 1H); 3.21 (dd, 1H); 3.38–3.58 (m, 2H); 3.64–3.78 (m, 1H); 3.93–4.02 (m, 1H); 4.15–4.22 (m, 2H); 7–83 (t, 1H); 8.04 (d, 1H); 8.25 (d, 1H); 8.64 (s, 1H); 9.40 (s, 1H).

The starting material was prepared as follows:

3-Carboxy-5-nitroisoquinoline was prepared from 3-carboxyisoquinoline using a method similar to that used for the preparation of 2-carboxy-8-nitroquinoline in example 10 (Yield: 93%).

NMR (DMSO-$d_6$+CF$_3$COOD): δ8.04 (t, 1H); 8.71 (d, 1H); 8.77 (d, 1H); 9.10 (s, 1H); 9.64 (s, 1H).

3-Allyloxycarbonyl-5-nitroisoquinoline was obtained from the product of the previous step using a similar method to that described for the preparation of 2-allyloxycarbonyl-6-nitroquinoline in example 7 (Yield: 45%).

NMR (DMSO-$d_6$): δ4.90–4.96 (m, 2H); 5.28–5.50 (m, 2H); 6.05–6.17 (m, 1H); 8.06 (t, 1H); 8.72 (d, 1H); 8.78 (d, 1H); 9.14 (s, 1H); 9.65 (s, 1H).

3-Allyloxycarbonyl-5-aminoisoquinoline was prepared using a similar method to that described for the preparation of 2-allyloxycarbonyl-6-aminoquinoline in example 7 (Yield: 90%).

NMR (DMSO-$d_6$): δ4.80–4.95 (m, 2H); 5.23–5.50 (m, 2H); 6.04–6.17 (m, 1H); 6.95 (d, 1H); 7.30 (d, 1H); 7.51 (t, 1H); 8.82 (s, 1H); 9.15 (s, 1H).

Preparation of the side-chain pyrrolidin-4-ylthioacetate:

(2S,4S) 1-Allyloxycarbonyl-2-(3-allyloxycarbonylisoquinol-5-ylcarbamoyl)pyrrolidin-4-ylthioacetate was prepared using a similar method to that described in example 7 (Yield: 71%).

NMR (DMSO-$d_6$+CD$_3$COOD): δ2.00–2.13 (m, 1H); 2.33 (s, 3H); 2.80–2.87 (m, 1H); 3.30–3.43 (m, 1H); 3.98–4.13 (m, 2H); 4.50–4.73 (m, 3H); 4.82–5.53 (m, 6H); 5.78–6.17 (m, 2H); 7.82 (t, 1H); 7.95–8.05 (m, 1H 8.06 (d, 1H); 8.73 (s, 1H); 9.39 (s, 1H). MS: (+ve FAB): 484

Preparation of the protected carbapenem:

Allyl (1R,5S,6S,8R,2'S,4'S)-2-(1-allyloxycarbonyl-2-(3-allyloxycarbonylisoquinol-5-ylcarbamoyl)pyrrolidin-4-ylthio)-6-(1-hydroxyethyl)-1-methylcarbapenem-3-carboxylate was prepared from the product of the previous step, using a similar method to that described in example 7 (Yield: 43%).

NMR (DMSO-$d_6$+CD$_3$COOD): δ1.10–1.23 (m, 6H); 1.95–2.10 (m, 1H); 2.82–2.97 (m, 1H); 3.25 (dd, 1H); 3.28–3.63 (m, 2H); 3.90–4.04 (m, 2H); 4.13–4.22 (m, 1H); 4.23–4.30 (m, 1H); 4.50–5.50 (m, 13H); 5.75–6.18 (m, 3H); 7.85 (t, 1H); 8.02–8.15 (m, 1H); 8.62–8.83 (m, 2H); 9.42 (s, 1H).

MS (+ve FAB): 691 (M+H).

We claim:

1. A compound of the formula (I)

wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
$P^1$ is of the formula:

and one or two of A,B,C,D,E,F,G and H are nitrogen and the remainder are CH; and $P^1$ is bonded to the nitrogen of the linking carbamoyl group by a carbon atom in either ring, is substituted by a carboxy group on a carbon atom in either ring, and is optionally substituted on one, two or three carbon atoms by a substituent selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, $C_{1-4}$alkylS(O)$_n$— (wherein n is 0–2), $C_{1-4}$alkanoylamino, $C_{1-4}$alkanoyl(N—$C_{1-4}$alkyl)amino, carbamoyl, $C_{2-6}$alkenyloxy, $C_{1-4}$alkylcarbamoyl and di-$C_{1-4}$alkylcarbamoyl; or a pharmaceutically acceptable salt or in vivo hydrolysable ester thereof.

2. The compound according to claim 1 wherein $R^2$ is methyl.

3. The compound according to claim 1 wherein $R^1$ is 1-hydroxyethyl.

4. The compound according to either claim 1 or claim 2 of the formula (IV):

wherein $P^1$, $R^3$, and optional substituents on $P^1$ are as defined in claim 1.

5. The compound according to claim 4 wherein optional substituents on $P^1$ are selected from halo, cyano, $C_{1-4}$alkyl, nitro, hydroxy, carboxy, $C_{1-4}$alkoxy, carbamoyl, amino, trifluoromethyl and allyloxy.

6. The compound according to claim 1 which is (1R,5S,6S,8R,2'S,4'S)-2-(2-(8-carboxyquinol-6-ylcarbamoyl)pyrrolidin-4-ylthio)-6-(1-hydroxyethyl)-1-methylcarbapenem-3-carboxylic acid; and
(1R,5S,6S,8R,2'S,4'S)-2-(2-(6-carboxyquinol-8-ylcarbamoyl)pyrrolidin-4-ylthio)-6-(1-hydroxyethyl)-1-methylcarbapenem-3-carboxylic acid;
(1R,5S,6S,8R,2'S,4'S)-2-(2-(7-carboxyquinol-5-ylcarbamoyl)pyrrolidin-4-ylthio)-6-(1-hydroxyethyl)-1-methylcarbapenem-3-carboxylic acid;

(1R,5S,6S,8R,2'S 4'S)-2-(2-(3-carboxyquinol-2-ylcarbamoyl)pyrrolidin-4-ylthio)-6-(1-hydroxyethyl)-1-methylcarbapenem-3-carboxylic acid:

(1R,5S,6S,8R,2'S,4'S)-2-(2-(2-carboxyquinol-4-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-6-allyloxyquinol-2-ylcarbamoyl)-pyrrolidin-4-ylthio)-6-(1-hydroxyethyl)-1-methylcarbapenem-3-carboxylic acid;

(1R,5S,6S,8R,2'S,4'S)-2-(2-(2-carboxyquinol-6-ylcarbamoyl)pyrrolidin-4-ylthio)-6-(1-hydroxyethyl)-1-methylcarbapenem-3-carboxylic acid;

(1R,5S,6S,8R,2'S 4'S)-2-(2-(4-carboxyquinol-8-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(4-carboxyquinol-5-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxyquinol-8-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxyquinol-5-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(4-carboxyquinol-2-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(7-carboxy-2,3-dimethylquinoxalin-5-ylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(4-carboxyquinazolin-2-ylcarbamoyl)-pyrrolidin-4-ylthio)-6-(1-hydroxyethyl)-1-methylcarbapenem-3-carboxylic acid;

(1R,5S,6S,8R,2'S,4'S)-2-(2-(3-carboxyisoquinol-5-ylcarbamoyl)-pyrrolidin-4-ylthio)-6-(1-hydroxyethyl)-1-methylcarbapenem-3-carboxylic acid;

and pharmaceutically-acceptable salts thereof.

7. A pharmaceutical composition which comprises a pharmaceutically effective amount of a compound according to claim 1 and a pharmaceutically acceptable carrier.

8. A method of treatment of a bacterial infection by administering an antibacterially effective amount of a compound according to claim 1 to a patient in need thereof.

* * * * *